(12) United States Patent
Park et al.

(10) Patent No.: US 10,576,404 B2
(45) Date of Patent: *Mar. 3, 2020

(54) AIR BLOWER APPARATUS

(71) Applicant: LG ELECTRONICS INC., Seoul (KR)

(72) Inventors: Daeyun Park, Seoul (KR); Byeongjo Ryoo, Seoul (KR); Seongho Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 108 days.

This patent is subject to a terminal disclaimer.

(21) Appl. No.: 15/642,494

(22) Filed: Jul. 6, 2017

(65) Prior Publication Data

US 2018/0008924 A1     Jan. 11, 2018

(30) Foreign Application Priority Data

Jul. 6, 2016 (KR) .................. 10-2016-0085336

(51) Int. Cl.
*A47K 10/06* (2006.01)
*F26B 21/00* (2006.01)
(Continued)

(52) U.S. Cl.
CPC ............ *B01D 46/0028* (2013.01); *A61L 9/22* (2013.01); *B01D 46/0002* (2013.01);
(Continued)

(58) Field of Classification Search
CPC . A47K 10/06; F26B 21/00; F26B 9/00; A61L 2/14; A61L 2/24; A61L 2/10;
(Continued)

(56) References Cited

U.S. PATENT DOCUMENTS 5,292,479 A * 3/1994 Haraga ................... A24F 19/00
 4/216
5,709,736 A * 1/1998 Fujimura ............... B01D 53/06
 55/400

(Continued)

FOREIGN PATENT DOCUMENTS

CN 2277501 4/1998
CN 103277846 9/2013
(Continued)

OTHER PUBLICATIONS

Chinese Office Action dated Jan. 30, 2019 issued in Application No. 201710546633.6 (English translation attached).
Chinese Office Action dated Aug. 30, 2019 issued in CN Application No. 201710546633.6.

*Primary Examiner* — Minh Chau T Pham
(74) *Attorney, Agent, or Firm* — Ked & Associates, LLP

(57) ABSTRACT

A bathroom management apparatus may include a case having an air suction port formed in an upper portion of a front surface thereof, a first air discharge port formed in a lower portion of the front surface thereof, and a second air discharge port formed in a lower surface thereof. A suction vane opens or closes the air suction port, and first and second discharge vanes opens or closes the first and second air discharge ports, respectively. A duct is provided in the case to connect the air suction port, the first air discharge port and the second air discharge port to one another. A blowing fan is provided in the duct to suck air through the air suction port and blow the air to the first air discharge port and the second air discharge port. A heater heats the air in the duct.

18 Claims, 25 Drawing Sheets

(51) Int. Cl.

| | |
|---|---|
| *F26B 9/00* | (2006.01) |
| *A61L 2/14* | (2006.01) |
| *A61L 2/24* | (2006.01) |
| *A61L 2/10* | (2006.01) |
| *A61L 9/18* | (2006.01) |
| *A61L 9/22* | (2006.01) |
| *B01D 45/14* | (2006.01) |
| *B01D 53/02* | (2006.01) |
| *F24F 3/14* | (2006.01) |
| *B01D 46/00* | (2006.01) |
| *B01D 46/42* | (2006.01) |
| *F24F 3/16* | (2006.01) |

(52) U.S. Cl.
CPC ..... *B01D 46/0045* (2013.01); *B01D 46/0047* (2013.01); *B01D 46/0061* (2013.01); *B01D 46/4263* (2013.01); *F24F 3/14* (2013.01); *A61L 2209/14* (2013.01); *B01D 46/0038* (2013.01); *B01D 2279/40* (2013.01); *B01D 2279/65* (2013.01); *F24F 2003/144* (2013.01); *F24F 2003/1682* (2013.01)

(58) Field of Classification Search
CPC .......... A61L 9/18; A61L 9/22; A61L 2209/14; B01D 45/14; B01D 53/02; B01D 46/0028; B01D 46/0002; B01D 46/0045; B01D 2279/65; F24F 3/14; F24F 3/166; F24F 2003/1982; F24F 2003/144
USPC ......... 55/385.1, 400, 403, 408, 472; 95/110, 95/113, 126; 96/74, 144, 146, 150; 1/1; 422/4, 5, 120–125
See application file for complete search history.

(56) References Cited

U.S. PATENT DOCUMENTS

| | | | | |
|---|---|---|---|---|
| 5,942,017 | A * | 8/1999 | Van Winkle, Sr. .... | B01D 46/00 55/385.1 |
| 6,129,781 | A * | 10/2000 | Okamoto ................ | B03C 3/12 96/25 |
| 6,217,439 | B1 * | 4/2001 | Janeling ............... | B60H 3/0641 454/158 |
| 7,171,761 | B1 * | 2/2007 | Hunts .................... | D06F 58/10 219/400 |
| 2006/0177356 | A1 * | 8/2006 | Miller ..................... | A61L 9/16 422/121 |
| 2008/0199367 | A1 * | 8/2008 | Lin .......................... | A61L 9/03 422/121 |
| 2015/0202559 | A1 * | 7/2015 | Oh ..................... | B01D 46/0065 55/289 |
| 2016/0184753 | A1 * | 6/2016 | Chu ..................... | B01D 46/002 96/74 |
| 2016/0246254 | A1 * | 8/2016 | Michibata ............. | G03G 21/206 |
| 2017/0314247 | A1 * | 11/2017 | Komatsu ................ | E03D 9/005 |
| 2018/0008924 | A1 * | 1/2018 | Park .................... | B01D 46/002 |
| 2018/0021468 | A1 * | 1/2018 | Kim .......................... | A61L 9/20 250/436 |
| 2018/0064296 | A1 * | 3/2018 | Jun ......................... | A47K 10/06 |
| 2018/0066867 | A1 * | 3/2018 | Kim ......................... | A61L 2/06 |

FOREIGN PATENT DOCUMENTS

| | | |
|---|---|---|
| CN | 204880411 | 12/2015 |
| CN | 105402883 | 3/2016 |
| JP | H 03271641 | 12/1991 |
| JP | 2009-039145 | 2/2009 |

* cited by examiner

AIR BLOWER APPARATUS

CROSS-REFERENCE TO RELATED APPLICATION

This application claims priority under 35 U.S.C. § 119 to Korean Patent Application No. 10-2016-0085336, filed on Jul. 6, 2016, in the Korean Intellectual Property Office, whose entire disclosure is hereby incorporated by reference.

BACKGROUND

1. Field

The present disclosure relates to a bathroom management apparatus, and more particularly to a bathroom management apparatus that is capable of exhibiting dehumidification and antibacterial effects.

2. Background

In general, a bathroom is a place used for clothes washing, face washing, hand washing, showering, urination/defecation, etc. Because a bathroom is the most humid place in the house, it is usually inhabited by a variety of fungi and bacteria and is prone to smelling badly.

In most cases, drying and deodorizing operations in a bathroom are performed only by a ventilation fan. However, the ventilation fan frequently operates improperly or does not exhibit sufficient performance for maintaining the entire bathroom in a dry state. Therefore, the bathroom may be easily contaminated due to inhabitation of fungi and bacteria attributable to remaining moisture.

In order to prevent a bathroom from being inhabited by fungi and bacteria, it is important to maintain the bathroom in a sufficiently dry state by removing moisture from the wet floor of the bathroom and from wet bathroom items, for example, a wet towel hung on a towel bar in the bathroom, at an early stage.

BRIEF DESCRIPTION OF THE DRAWINGS

The embodiments will be described in detail with reference to the following drawings in which like reference numerals refer to like elements wherein.

DETAILED DESCRIPTION

Figure 1:
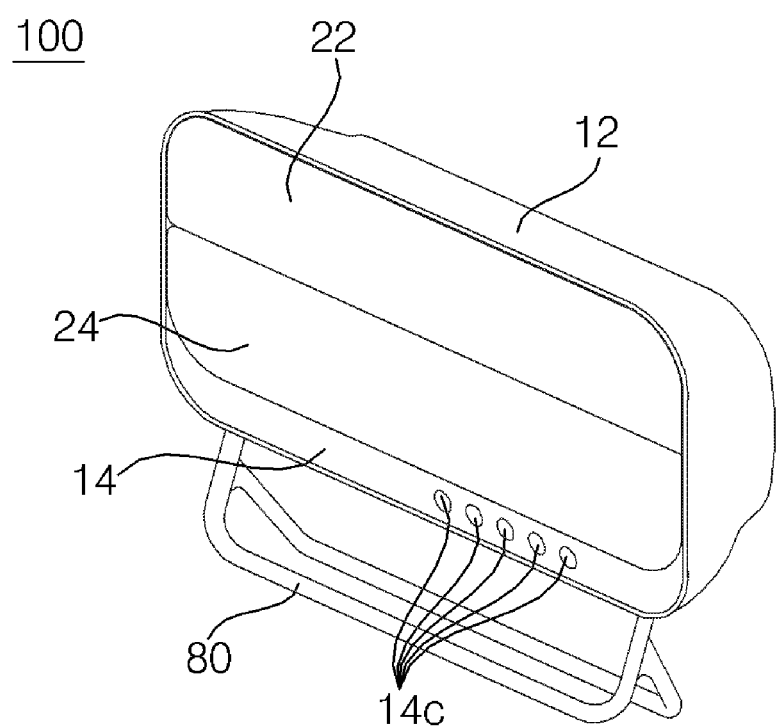
FIG. 1 is a view illustrating a bathroom management apparatus according to an embodiment of the present disclosure.
Figure 2:
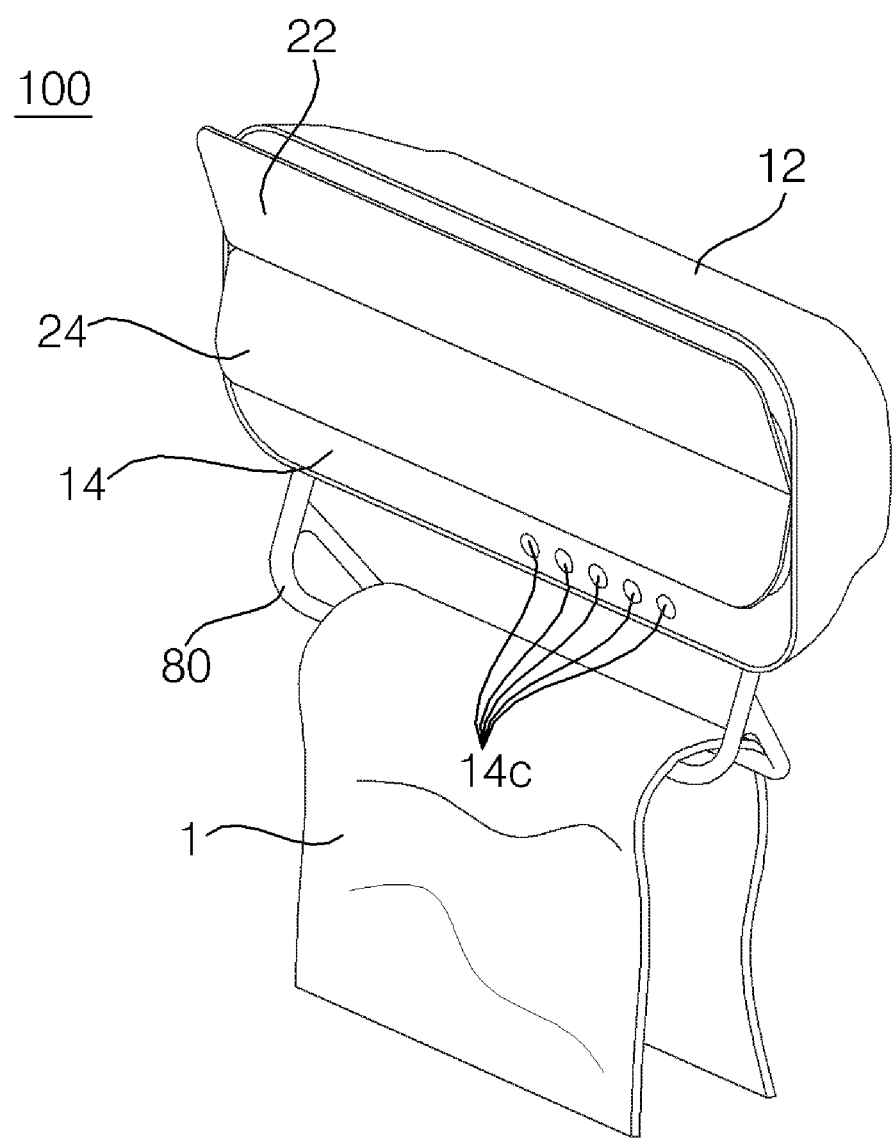
FIG. 2 is a view illustrating the state in which a suction vane and a first discharge vane shown in FIG. 1 are open.

Referring to FIGS. 1 to 6, a bathroom management apparatus 100 according to the embodiment of the present disclosure is configured to be installed on the wall of a bathroom, and includes a case 12 and 14 defining the external appearance thereof, a suction vane 22 and a first discharge vane 24, which are rotatably coupled to the front surface of the case 12 and 14, a duct 30 mounted in the case 12 and 14, a second discharge vane 26 rotatably coupled to the duct 30, a blowing fan 40 mounted in the duct 30, and a heater 50 for heating air in the duct 30.

The case 12 and 14 has an air suction port 14a formed in the upper portion of the front surface thereof to suck air in the bathroom thereinto, and a first air discharge port 14b formed in the lower portion of the front surface thereof to discharge the air heated by the heater 50. The case 12 and 14 further has a second air discharge port 12a formed in the lower surface thereof to discharge the air heated by the heater 50.

The case 12 and 14 includes an outer case 12 and an inner case 14. The outer case 12 has a substantially hexahedral shape having an empty inner space and an open front surface. The second air discharge port 12a is formed in the lower surface of the outer case 12 so as to communicate with the empty inner space of the outer case 12. The outer case 12 defines the upper surface, the lower surface, the left surface, the right surface and the rear surface of the case 12 and 14.

The inner case 14 is inserted into the outer case 12 through the open front surface of the outer case 12. The inner case 14 inserted into the outer case 12 is positioned near the front surface of the outer case 12 so as to form a space for receiving the duct 30 mounted therein between the inner case 14 and the rear surface of the outer case 12. The inner case 14 serves as the front surface of the case 12 and 14.

When the suction vane 22 and the first discharge vane 24 are in a closed state, as shown in FIG. 1, the lower end portion of the inner case 14 is exposed outside. The exposed lower end portion of the inner case 14 is provided with input buttons 14c, which are configured to be pushed by the user. The user is capable of operating the bathroom management apparatus 100 in a desired mode by pushing the input buttons 14c.

The inner case 14 is divided from top to bottom into an upper portion 14d, an intermediate portion 14e, and a lower portion 14f. The air suction port 14a is formed in the upper portion 14d of the inner case 14, and the first air discharge port 14b is formed in the lower portion 14f of the inner case 14. The intermediate portion 14e refers to the portion of the inner case 14 that corresponds to the region between the air suction port 14a and the first air discharge port 14b.

The upper portion 14d of the inner case 14 includes partition plates 14g for partitioning the air suction port 14a into a plurality of sections.

An illumination device 15 for generating light is mounted to the intermediate portion 14e of the inner case 14. The illumination device 15 may include a lens cover 15a coupled to the inner case 14 and a plurality of light-emitting diodes (LEDs) provided in the lens cover 15a. Alternatively, the illumination device 15 may include a light bulb instead of the LEDs. When the suction vane 22 and the air suction port 14a are in an open state, the illumination device 15 is exposed through the upper space formed between the inner case 14 and the suction vane 22. Therefore, when the illumination device 15 generates light in the state in which the suction vane 22 and the air suction port 14a are open, the light generated by the illumination device 15 is radiated to the interior of the bathroom through the upper space formed between the inner case 14 and the suction vane 22.

A filter 60 is mounted to the front surface of the upper portion 14d of the inner case 14. Specifically, the filter 60 is mounted to the air suction port 14a, and removes bad smells, dusts and bacteria from the air in the bathroom. The filter 60 is configured as an antibacterial filter, which includes a photocatalytic coating layer that is activated by the light generated by the illumination device 15.

A reflector 23 is coupled to the rear surface of the suction vane 22 in order to reflect the light generated by the illumination device 15 to the filter 60. The reflector 23 may be embodied as a mirror. The photocatalytic layer of the filter 60 is activated by the light that is generated by the illumination device 15 and is reflected by the reflector 23.

In order to ensure good performance of the filter 60 in spite of the repeated use thereof, a photocatalytic material is coated on the surface of the filter 60, and this photocatalytic material is activated by the light from an external light source (e.g. an illumination device mounted in the bathroom) or the light from the illumination device 15 of the bathroom management apparatus. Through the activation of the photocatalytic material, odor particles collected in the filter 60 are decomposed into an odorless substance. This deodorizing performance of the filter 60 is steadily maintained by the photocatalytic material coated thereon.

A discharge grill 18 is mounted to the front surface of the lower portion 14f of the inner case 14. Specifically, the discharge grill 18 is mounted to the first air discharge port 14b in order to discharge the air in the duct 30 from the first air discharge port 14b to the interior of the bathroom.

The suction vane 22 is mounted to the front surface of the case 12 and 14 in order to open or close the air suction port 14a. The first discharge vane 24 is mounted to the front surface of the case 12 and 14 in order to open or close the first air discharge port 14b. The second discharge vane 26 is mounted to the duct 30 in order to open or close the second air discharge port 12a.

The suction vane 22 is rotatably coupled at the lower end thereof to the intermediate portion 14e of the inner case 14. When the suction vane 22 rotates about the lower end thereof such that the upper end thereof moves away from the inner case 14, the air suction port 14a is opened. From this open state, when the suction vane 22 rotates about the lower end thereof such that the upper end thereof moves close to the inner case 14, the air suction port 14a is closed.

The first discharge vane 24 is provided below the suction vane 22. The upper end of the first discharge vane 24 is located adjacent to the lower end of the suction vane 22. The first discharge vane 24 is rotatably coupled at the upper end thereof to the intermediate portion 14e of the inner case 14. When the first discharge vane 24 rotates about the upper end thereof such that the lower end thereof moves away from the inner case 14, the first air discharge port 14b is opened. From this open state, when the first discharge vane 24 rotates about the upper end thereof such that the lower end thereof moves close to the inner case 14, the first air discharge port 14b is closed.

When the air suction port 14a and the first air discharge port 14b are intended to be opened, the suction vane 22 and the first discharge vane 24 are rotated to a predetermined angle, e.g. 35 degrees, with respect to the inner case 14. When the suction vane 22 and the first discharge vane 24 are in an open state, the air in the bathroom moves into the air suction port 14a via the upper space between the suction vane 22 and the inner case 24, and is sucked into the duct 30. The air sucked into the duct 30 moves to the lower space between the first discharge vane 24 and the inner case 14 via the first air discharge port 14b, and is discharged to the interior of the bathroom. Since an air vent is typically mounted at the top of the bathroom, it is advantageous to the circulation of warm air in the bathroom and drying of the floor of the bathroom to discharge warm air from the duct 30 in the downward direction. During the operation of the bathroom management apparatus 100, the direction in which air flows is adjusted by rotation of at least one of the suction vane 22 and the first discharge vane 24. While the bathroom management apparatus 100 is not operating, both the suction vane 22 and the first discharge vane 24 are closed to minimize the size of the bathroom management apparatus 100 in the forward/backward direction, thereby preventing the user from bumping into the same when the user moves in the bathroom.

The duct 30 is mounted in the case 12 and 14. Specifically, the duct 30 is mounted in the space between the rear surface of the inner case 14 and the outer case 12. The duct 30 connects the air suction port 14a, the first air discharge port 14b and the second air discharge port 12a to one another.

The duct 30 includes an open front-upper portion and an open front-lower portion, which are spaced apart from each other, and an open bottom portion. The open front-upper portion and the open front-lower portion of the duct 30 protrude in the forward direction such that a backwardly recessed space 34 is formed in the front-intermediate portion of the duct 30, which is defined between the open front-upper portion and the open front-lower portion. The open front-upper portion of the duct 30 is coupled to the rear surface of the inner case 14 so as to correspond to the air suction port 14a. The open front-lower portion of the duct 30 is coupled to the rear surface of the inner case 14 so as to correspond to the first air discharge port 14b. The open bottom portion of the duct 30 is coupled to the lower surface of the outer case 12 so as to correspond to the second air discharge port 12a.

The duct 30 includes a main flow path 31 connected to the air suction port 14a, a first sub-flow path 32 branched from the main flow path 31 and connected to the first air discharge port 14b, and a second sub-flow path 33 branched from the main flow path 31 and connected to the second air discharge port 12a. The main flow path 31 is positioned above the first sub-flow path 32 and the second sub-flow path 33. The main flow path 31 is coupled to the rear surface of the upper portion 14d of the inner case 14 so as to correspond to the air suction port 14a. The first sub-flow path 32 is branched from the lower end of the main flow path 31 and is coupled to the rear surface of the lower portion 14f of the inner case 14 so as to correspond to the first air discharge port 14b. The second sub-flow path 33 is branched from the lower end of the main flow path 31 and is coupled to the lower surface of the outer case 12 so as to correspond to the second air discharge port 12a.

The blowing fan 40 is mounted in the main flow path 31. The blowing fan 40 is formed lengthwise in the lateral direction, and the longitudinal direction thereof is the rotational axis direction. That is, the blowing fan 40 is embodied as a tangential fan, which sucks or discharges air in the radial direction. The duct 30 has insertion holes 36 formed in the left-upper and right-upper portions of the main flow path 31, into which the left and right ends of the blowing fan 40 are respectively inserted. The blowing fan 40 is mounted in the upper portion of the main flow path 31 and is located behind the air suction port 14a.

In addition, the heater 50 is mounted in the main flow path 31. The heater 50 is embodied as an electric heater for generating heat using electric power. In the main flow path 31, the blowing fan 40 is located upstream of the heater 50, and the heater 50 is located downstream of the blowing fan 40. If the blowing fan 40 is located downstream of the heater 50, the blowing fan 40 sucks warm air that has been heated by the heater 50, which may cause thermal deformation of the blowing fan 40. Accordingly, it is preferable for the blowing fan 40 to be located upstream of the heater 50.

A plurality of ionizers 70 is mounted to the rear surface of the duct 30 that defines the main flow path 31. The ionizers 70 emit a large number of positive ions and negative ions (hereinafter, referred to as "ions") toward the interior of the duct 30. Therefore, the ions emitted from the ionizers 70 are contained in the air discharged through the first air discharge port 14b and the second air discharge port 12a. The ions introduced into the bathroom serve to react with microbes and bacteria in the bathroom and to kill them by destroying their DNA. Further, the ions also serve to react with fungi and to inhibit the growth thereof. The duct 30 has communication holes 37 formed in the rear surface thereof that defines the main flow path 31, in order to communicate with the ionizers 70. The ionizers 70 are arranged in the lateral direction while being spaced apart from each other. The communication holes 37 are formed in the same number as the ionizers 70.

The ionizers 70 are provided below the heater 50, and are located as close to the first sub-flow path 32 and the second sub-flow path 33 as possible. The reason for this is that when there are no obstacles or little resistance in the passage of the ion particles emitted from the ionizers 70, the viability of the ions increases. The air introduced into the main flow path 31 via the air suction port 14a by the suction force of the blowing fan 40 is moved to the heater 50 by the blowing fan 40, and is converted into warm air by being heated by the heater 50. Subsequently, the warm air receives the ions emitted from the ionizers 70, and the warm air containing the ions is discharged to the interior of the bathroom via one of the first air discharge port 14b and the second air discharge port 12a.

In addition, a flow-path-switching damper 35 is mounted in the duct 30. The flow-path-switching damper 35 is rotatably mounted to a portion of the duct 30 that is located below the ionizers 70. The flow-path-switching damper 35 serves to enable the main flow path 31 to selectively communicate with one of the first sub-flow path 32 and the second sub-flow path 33.

When the first discharge vane 24 opens the first air discharge port 14b, the flow-path-switching damper 35 enables the first sub-flow path 32 to communicate with the main flow path 31. When the second discharge vane 26 opens the second air discharge port 12a, the flow-path-switching damper 35 enables the second sub-flow path 33 to communicate with the main flow path 31. When the flow-path-switching damper 35 enables the first sub-flow path 32 to communicate with the main flow path 31, the air in the duct 30 is discharged to the interior of the bathroom via the first air discharge port 14b. When the flow-path-switching damper 35 enables the second sub-flow path 33 to communicate with the main flow path 31, the air in the duct 30 is discharged to the interior of the bathroom via the second air discharge port 12a.

In addition, a rack unit 80 is mounted to the bottom surface of the case 12 and 14. Specifically, the rack unit 80 is coupled to a portion of the bottom surface of the outer case 12 that corresponds to the second air discharge port 12a. The rack unit 80 is secured to the bottom surface of the outer case 12 so as to extend outwards from the bottom surface of the outer case 12. Alternatively, the rack unit 80 may be mounted such that it is accommodated in the inner space of the outer case 12, which is formed behind the duct 30, when not in use and such that it protrudes outward from the bottom surface of the outer case 12 when in use.

A towel 1 or the like may be hung on the portion of the rack unit 80 that is aligned with the second air discharge port 12a. After washing the face or hands or showering, the user may dry himself/herself with the towel 1 and may hang the wet towel 1 on the rack unit 80. The wet towel 1, which is hung on the rack unit 80, is dried and sterilized by the air discharged through the second air discharge port 12a. In order to effectively dry and sterilize the towel 1 hung on the rack unit 80, it is preferable for the second air discharge port 12a to be formed so as to discharge air toward the rack unit 80.

That is, the air discharged through the first air discharge port 14b functions to dry and sterilize the interior of the bathroom, and the air discharged through the second air discharge port 12a functions to dry and sterilize the towel 1 or the like.

The wet towel 1 or other wet bathroom items may also be inhabited by microbes and bacteria. In this case, the towel 1 may stink badly, or the contaminated towel 1 may become a vector that transfers contaminants therefrom to other users. Further, in many cases, the towel 1 may be repeatedly used for face washing or other activities in the bathroom for one or more days. The wet towel 1 in the bathroom, which is a very humid place, provides optimum growth conditions for bacteria that live by obtaining nutrients from skin tissues separated from the skin surface of the user.

The bathroom management apparatus 100 is capable of sterilizing the wet towel 1 or other bathroom items using ions emitted from the ionizers 70, and the sterilization efficiency may be increased to 99% when warm air heated by the heater 50 is used together with the ions. This effect is realized by a mechanism whereby the moisture present in the towel 1 is completely evaporated by increasing the difference between the partial pressure of water vapor in the wet towel 1 and the partial pressure of water vapor in the high-temperature and low-humidity air. The embodiment may be constructed such that the operation of the heater 50 is restricted in the final stage of sterilization in order to greatly reduce energy consumption.

Meanwhile, the outer case 12 may be modified such that it is expanded further to the left or to the right in order to provide a toothbrush accommodation unit at the expanded portion of the outer case 12. Further, an additional flow path may be formed so as to be branched from a portion of the main flow path 31 that is positioned below the ionizers 70 and to be connected to the toothbrush accommodation unit. Accordingly, the air, in which the ions emitted from the ionizers 70 are contained, is introduced into the toothbrush accommodation unit, thereby rapidly drying and sterilizing the toothbrush accommodated in the toothbrush accommodation unit. Depending on the situation, the heater 50 may be driven together with the ionizers 70 so that warm air containing ions is supplied to the toothbrush accommodation unit, thereby more effectively drying and sterilizing the toothbrush. As such, in the case in which an additional flow path is branched from the main flow path 31 to the toothbrush accommodation unit, it is preferable to mount an additional damper in the duct 30 in order to open or close the additional flow path connected to the toothbrush accommodation unit. In addition, a toothbrush holder, on which the toothbrush is hung, may be provided in the toothbrush accommodation unit. In addition, an ultraviolet-light-emitting diode (UV LED) for sterilizing the toothbrush may be mounted in the toothbrush accommodation unit.

A controller 90 is received in the backwardly recessed space 34 that is formed in the front-intermediate portion of the duct 30. The controller 90 serves to control the operation of the bathroom management apparatus 100. The controller 90 may be coupled to the duct 30 in a manner of being inserted into the space 34 in the duct 30 or may be coupled to the rear surface of the inner case 14. In addition, at least one motor 200 for driving the suction vane 22 and the first discharge vane 24 may be inserted into the space 34 in the duct 30 and may be coupled to the rear surface of the inner case 14. In addition, a motor (not shown) for driving the second discharge vane 26 may be coupled to the duct 30 in a manner of being inserted into the space 34 in the duct 30.

Figure 3:
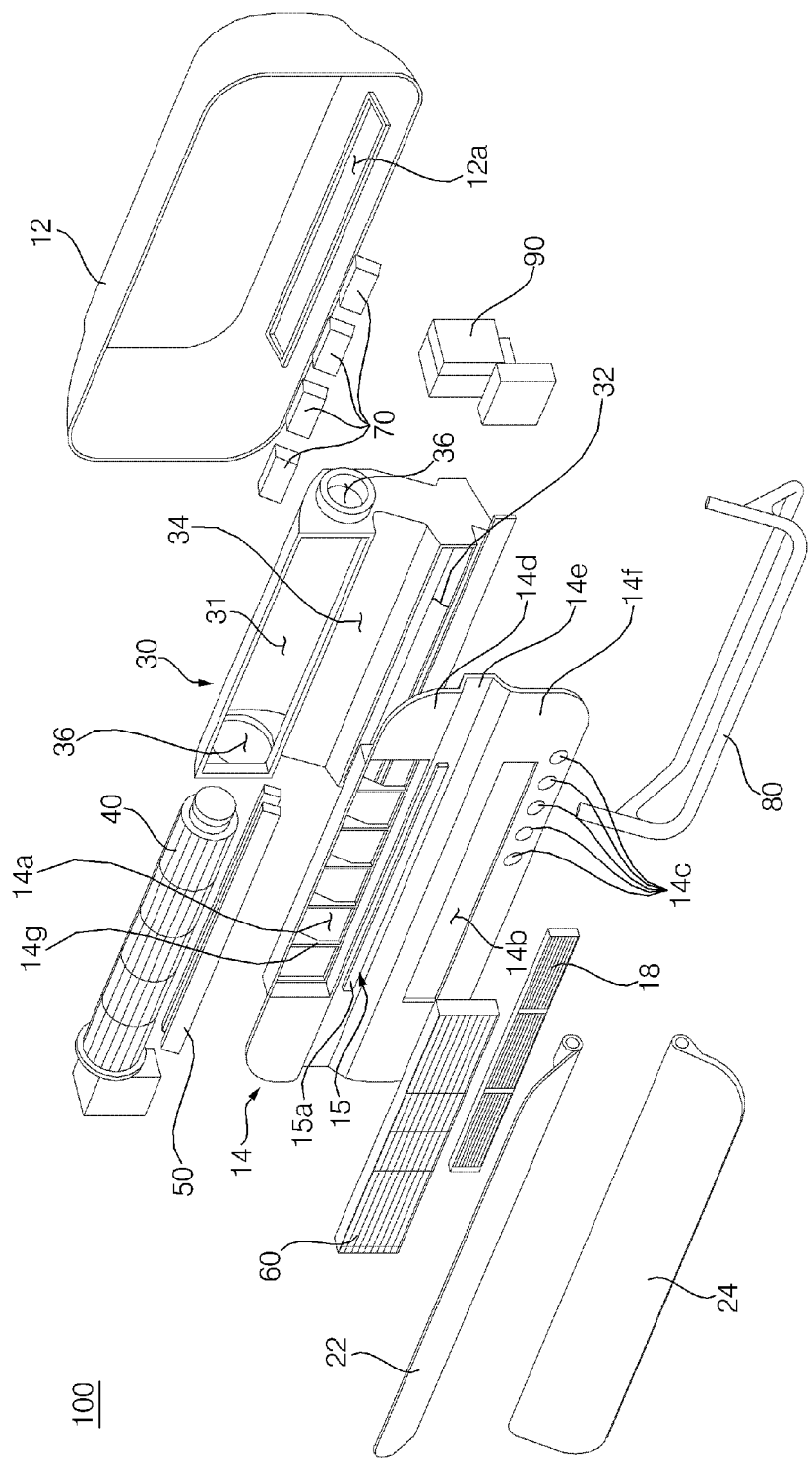
FIG. 3 is an exploded perspective view of FIG. 1.
Figure 7:
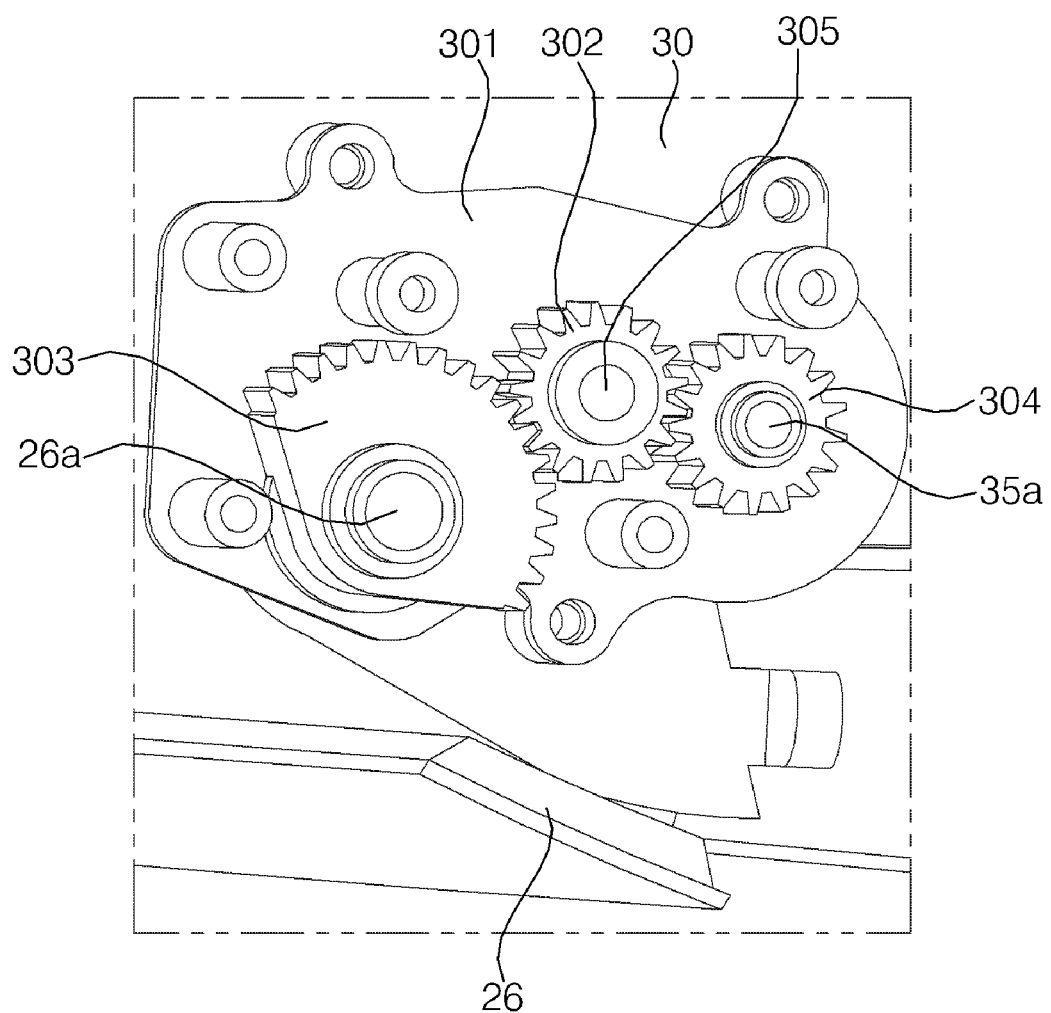
FIG. 7 is a view illustrating the interior of a first gearbox mounted to a portion of a duct shown in FIG. 3.

FIG. 7 is a view illustrating the interior of a first gearbox mounted to a portion of the duct shown in FIG. 3.

Referring to FIGS. 3 to 7, a first gearbox 301 is mounted to a portion of the duct 30. A motor (not shown), which is connected to the first gearbox 301, is received in the space 34 in the duct 30 that is opposite the portion to which the first gearbox 301 is mounted. A first driving gear 302, a first driven gear 303 and a second driven gear 304 are rotatably mounted in the first gearbox 301. The first driving gear 302 is interposed between the first driven gear 303 and the second driven gear 304 and is engaged with the first driven gear 303 and the second driven gear 304. That is, the first driven gear 303 is provided at one side of the first driving gear 302 so as to be engaged with the same, and the second driven gear 304 is provided at the opposite side of the first driving gear 302 so as to be engaged with the same.

A rotating shaft 305 of the motor received in the space 34 in the duct 30 penetrates the portion of the duct 30 and the first gearbox 301, and is coupled to the first driving gear 302. The first driven gear 303 is coupled to a rotating shaft 26a of the second discharge vane 26, and the second driven gear 304 is coupled to a rotating shaft 35a of the flow-path-switching damper 35. Therefore, when the motor operates, the first driving gear 302 is rotated simultaneously with the rotating shaft 305 of the motor by the driving force of the motor. At the same time, since the first driven gear 303 and the second driven gear 304 are rotated, the second discharge vane 26 and the flow-path-switching damper 35 are also rotated simultaneously.

That is, when the second air discharge port 12a is in the closed state by the second discharge vane 26, the flow-path-switching damper 35 enables the main flow path 31 and the first sub-flow path 32 to communicate with each other, and blocks communication between the main flow path 31 and the second sub-flow path 33. In this state, when the second discharge vane 26 is rotated to open the second air discharge port 12a, the flow-path-switching damper 35 is rotated together with the second discharge vane 26, thereby blocking communication between the main flow path 31 and the first sub-flow path 32 and allowing communication between the main flow path 31 and the second sub-flow path 33.

The gear ratio of the first driven gear 303 to the second driven gear 304 is set to be 2:1.

As described above, the bathroom management apparatus 100 according to the embodiment of the present disclosure is characterized in that the second discharge vane 26 and the flow-path-switching damper 35 are driven simultaneously by a single motor.

The second discharge vane 26 opens the second air discharge port 12a, and the flow-path-switching damper 35 allows communication between the main flow path 31 and the second sub-flow path 33, only when the bathroom management apparatus 100 operates in an antibacterial-drying mode with respect to wet bathroom items, e.g. the towel 1 hung on the rack unit 80. At this time, the first air discharge port 14b is in the closed state by the first discharge vane 24, and the communication between the main flow path 31 and the first sub-flow path 32 is in the blocked state by the flow-path-switching damper 35.

When the bathroom management apparatus 100 operates in modes other than the antibacterial-drying mode with respect to wet bathroom items, e.g. the towel 1 hung on the rack unit 80, the first discharge vane 24 opens the first air discharge port 14b, and the flow-path-switching damper 35 allows communication between the main flow path 31 and the first sub-flow path 32. At this time, the second air discharge port 12a is in the closed state by the second discharge vane 26, and the communication between the main flow path 31 and the second sub-flow path 33 is in the blocked state by the flow-path-switching damper 35.

Figure 8:
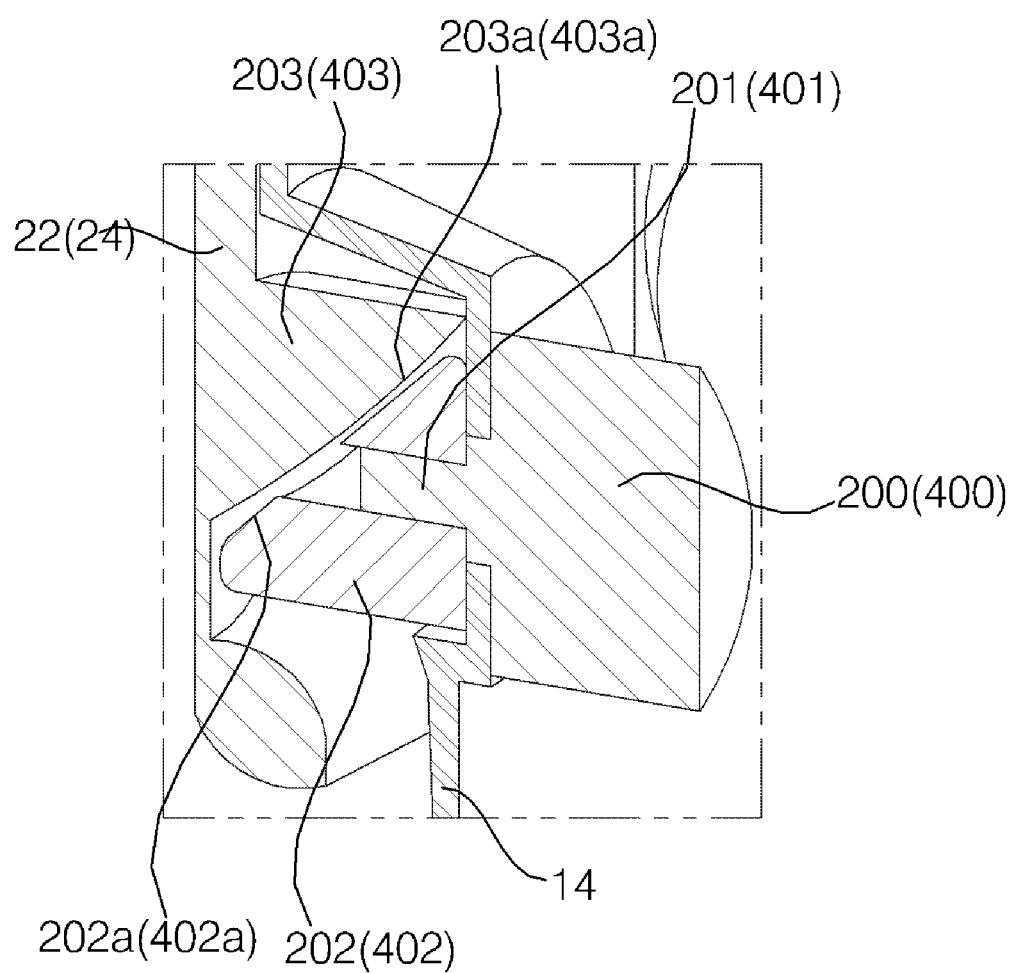
FIG. 8 is a cutaway perspective view of an embodiment illustrating the state in which the suction vane and the first discharge vane are closed.
Figure 9:
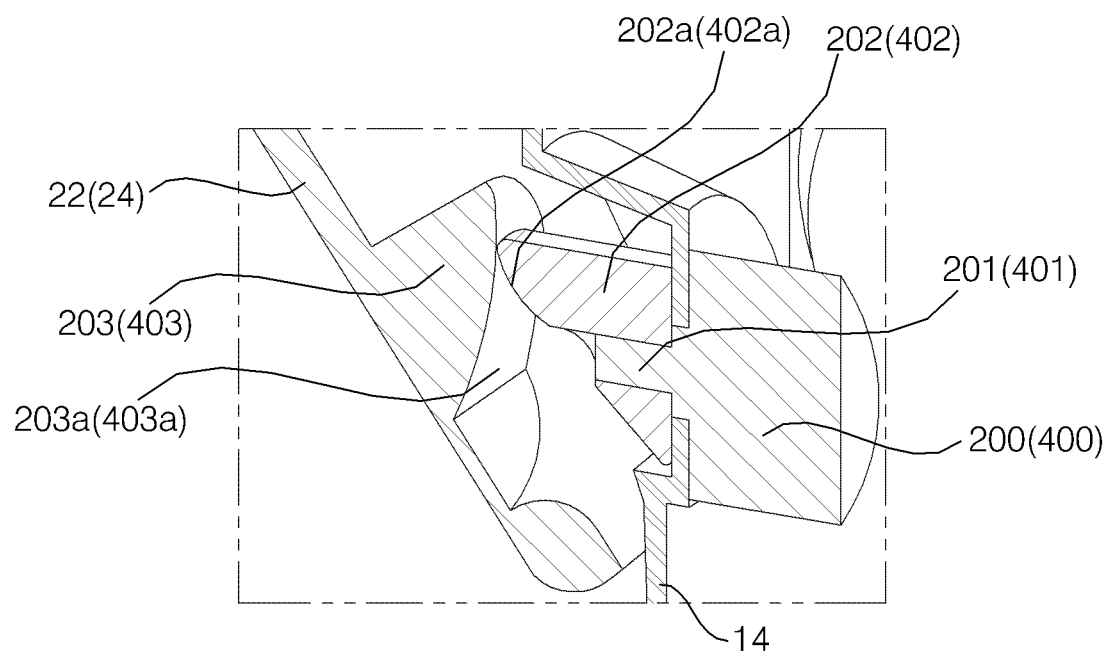
FIG. 9 is a cutaway perspective view of an embodiment illustrating the state in which the suction vane and the first discharge vane are open.

FIG. 8 is a cutaway perspective view of an embodiment illustrating the state in which the suction vane and the first discharge vane are closed, and FIG. 9 is a cutaway perspective view of an embodiment illustrating the state in which the suction vane and the first discharge vane are open.

Referring to FIGS. 8 and 9, the suction vane 22 and the first discharge vane 24 are rotated to be opened or closed by opening/closing mechanisms having the same structure. Therefore, only the suction vane 22 and the suction vane opening/closing mechanism for opening or closing the suction vane 22 are illustrated in FIGS. 8 and 9, and the reference numerals indicating the first discharge vane 24 and the first discharge vane opening/closing mechanism for opening or closing the first discharge vane 24 are put in parentheses.

A first driving motor 200 is mounted to the rear surface of the inner case 14. A rotating shaft 201 of the first driving motor 200 penetrates the inner case 14 and protrudes to a region ahead of the inner case 14. A first cam 202 is coupled to the rotating shaft 201 of the first driving motor 200. The first cam 202 is coupled to the portion of the rotating shaft 201 that protrudes to a region ahead of the inner case 14 after penetrating the inner case 14, and is therefore located ahead of the inner case 14. The first cam 202 includes a first inclined portion 202a that is formed in the front surface thereof in an inclined manner. A second cam 203 is formed at the lower end portion of the rear surface of the suction vane 22 so as to protrude backwards. The second cam 203 includes a second inclined portion 203a that is formed in the rear surface thereof so as to correspond to the first inclined portion 202a.

By virtue of the first inclined portion 202a and the second inclined portion 203a, as the first cam 202 is rotated together with the rotating shaft 201 of the first driving motor 200 by the driving force of the first driving motor 200, the first cam 202 pushes the second cam 203 in the forward direction, thereby opening the suction vane 22. In the state in which the suction vane 22 is open, when the first driving motor 200 rotates to a position at which the suction vane 22 is closed, the suction vane 22 is closed by the restoring force of a first return spring (not shown).

In addition, a second driving motor 400 is mounted to the rear surface of the inner case 14. A rotating shaft 401 of the second driving motor 400 penetrates the inner case 14 and protrudes to a region ahead of the inner case 14. A third cam 402 is coupled to the rotating shaft 401 of the second driving motor 400. The third cam 402 is coupled to the portion of the rotating shaft 401 that protrudes to a region ahead of the inner case 14 after penetrating the inner case 14, and is therefore located ahead of the inner case 14. The third cam 402 includes a third inclined portion 402a that is formed in the front surface thereof in an inclined manner. A fourth cam 403 is formed at the upper end portion of the rear surface of the first discharge vane 24 so as to protrude backwards. The fourth cam 403 includes a fourth inclined portion 403a that is formed in the rear surface thereof so as to correspond to the third inclined portion 402a.

By virtue of the third inclined portion 402a and the fourth inclined portion 403a, as the third cam 402 is rotated together with the rotating shaft 401 of the second driving motor 400 by the driving force of the second driving motor 400, the third cam 402 pushes the fourth cam 403 in the forward direction, thereby opening the first discharge vane 24. In the state in which the first discharge vane 24 is open, when the second driving motor 400 rotates to a position at which the first discharge vane 24 is closed, the first discharge vane 24 is closed by the restoring force of a second return spring (not shown).

As described above, since the second cam 203 formed at the suction vane 22 has the second inclined portion 203a formed in the rear surface thereof and the first cam 202 coupled to the rotating shaft 201 of the first driving motor 200 has the first inclined portion 202a formed in the front surface thereof, the user is capable of manually opening the suction vane 22. Similarly, since the fourth cam 403 formed at the first discharge vane 24 has the fourth inclined portion 403a formed in the rear surface thereof and the third cam 402 coupled to the rotating shaft 401 of the second driving motor 400 has the third inclined portion 402a formed in the front surface thereof, the user is capable of manually opening the first discharge vane 24.

This enables the user to easily replace the filter 60 and to easily clean the interior of the duct 30 and the blowing fan 40 merely by manually opening the suction vane 22 and the first discharge vane 24. During the operation of the bathroom management apparatus 100 (e.g. the operation of the blowing fan), if the user manually opens at least one of the suction vane 22 and the first discharge vane 24, a hall sensor (not shown) detects the opening of at least one of the suction vane 22 and the first discharge vane 24 and transmits the detection result to the controller 90. In response to the detection result, the controller 90 may stop the operation of the bathroom management apparatus 100.

In the above-described structure, the suction vane opening/closing mechanism and the first discharge vane opening/closing mechanism respectively include the first driving motor 200 and the second driving motor 400. That is, two motors 200 and 400 are required to open or close the suction vane 22 and the first discharge vane 24. The structure of opening or closing the suction vane 22 and the first discharge vane 24 using a single motor will now be described with reference to FIGS. 10 to 12.

Figure 10:
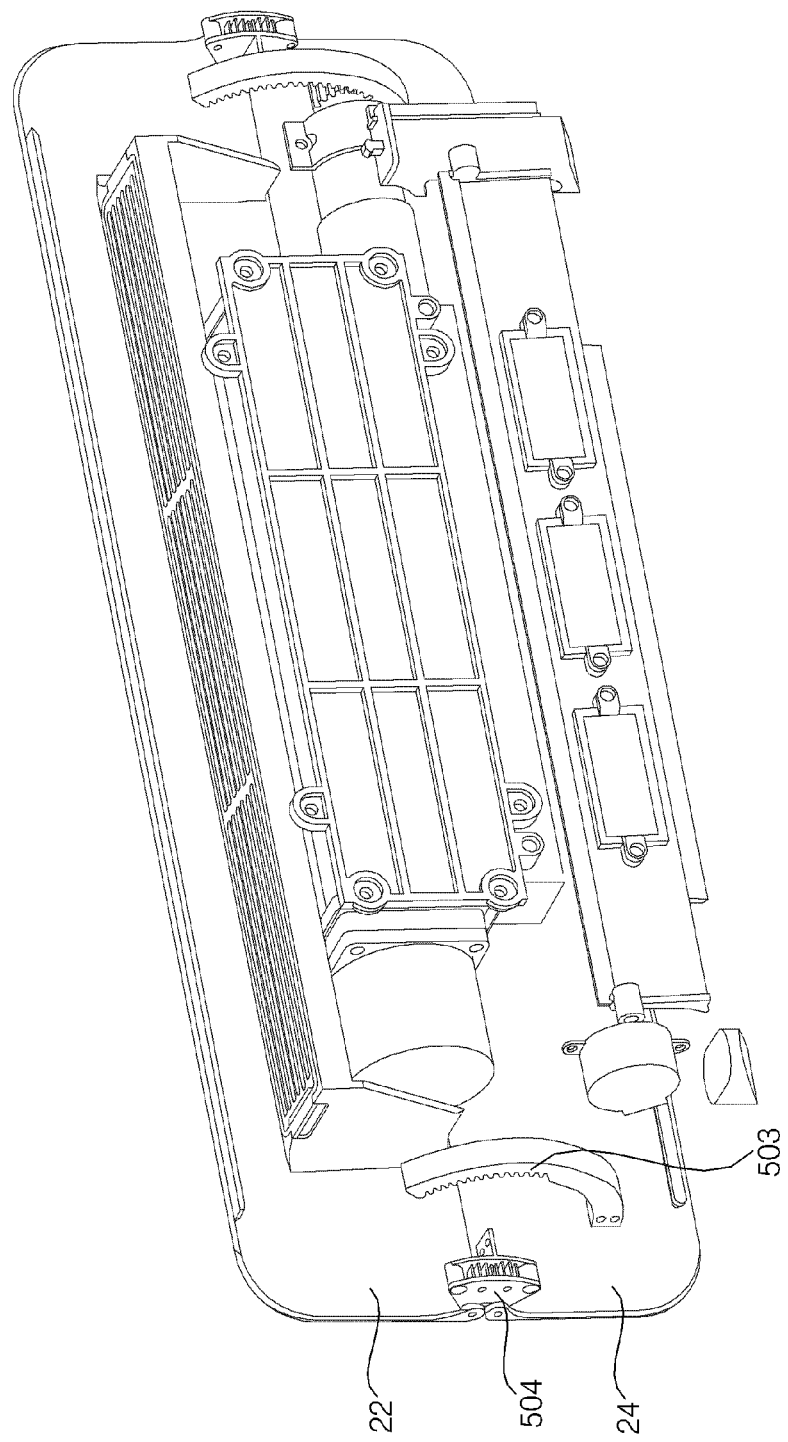
FIG. 10 is a perspective view of another embodiment illustrating the state in which the suction vane and the first discharge vane are closed.
Figure 11:
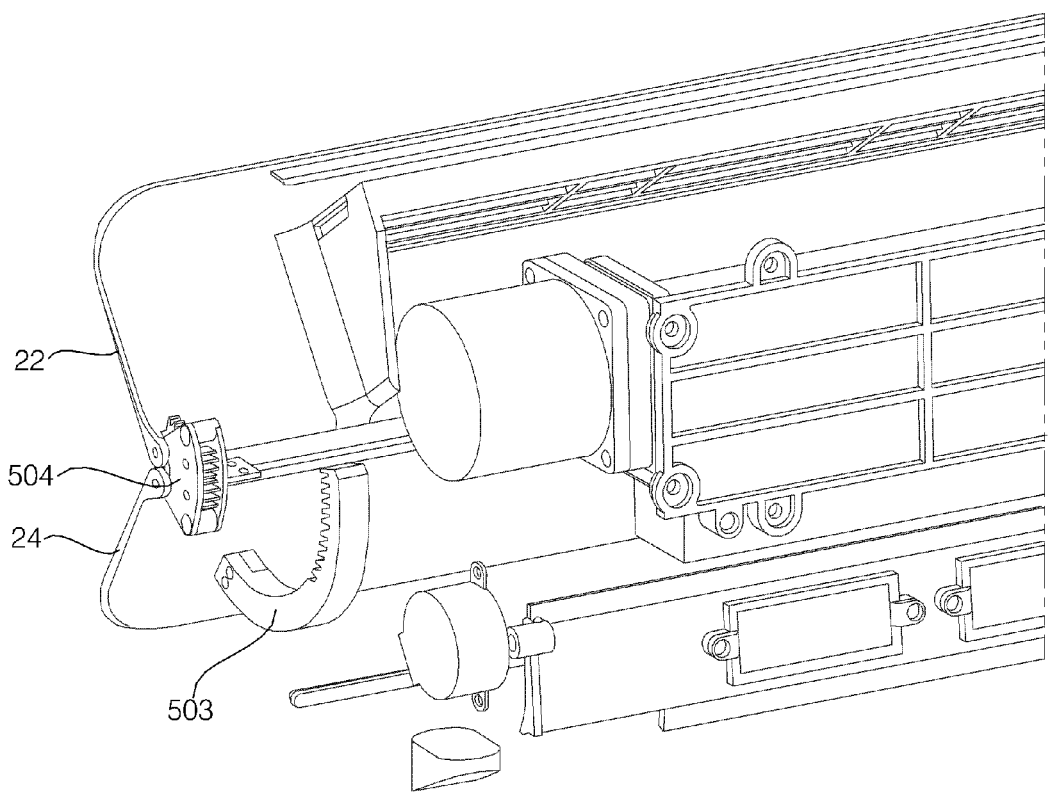
FIGS. 11 and 12 are perspective views of another embodiment illustrating the state in which the suction vane and the first discharge vane are open.
Figure 12:
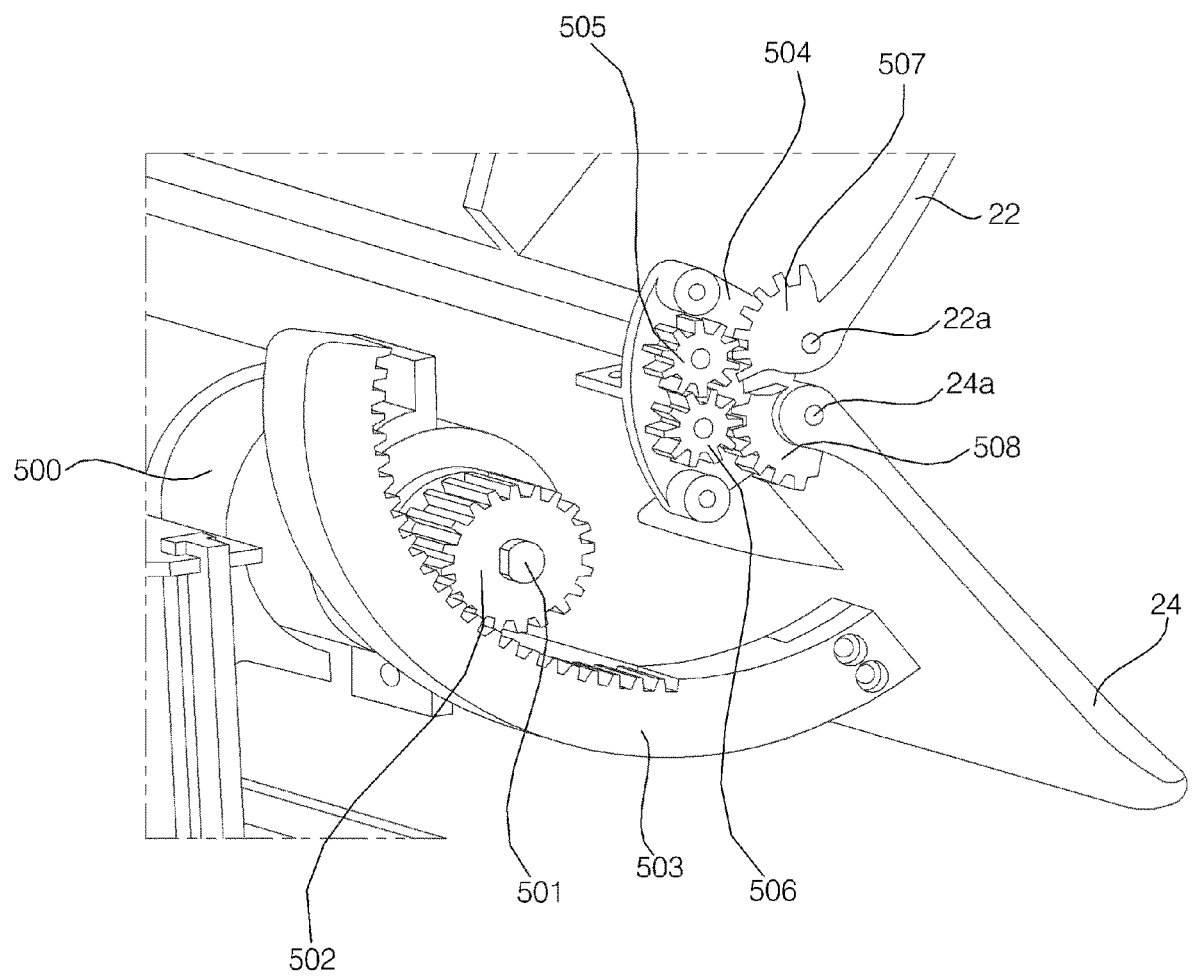

FIG. 10 is a perspective view of another embodiment illustrating the state in which the suction vane and the first discharge vane are closed, and FIGS. 11 and 12 are perspective views of another embodiment illustrating the state in which the suction vane and the first discharge vane are open.

Referring to FIGS. 10 to 12, the bathroom management apparatus 100 according to the embodiment of the present disclosure includes a driving motor 500, a driving gear 502 coupled to a rotating shaft 501 of the driving motor 500, an internal gear 503 coupled to the rear surface of the first discharge vane 24 and engaged with the driving gear 502, a gearbox 504, a first gear 505 rotatably mounted in the gearbox 504, a second gear 506 rotatably mounted in the gearbox 504 and engaged with the first gear 505, a third gear 507 coupled to a rotating shaft 22a of the suction vane 22 and engaged with the first gear 505, and a fourth gear 508 coupled to a rotating shaft 24a of the first discharge vane 24 and engaged with the second gear 506.

The driving motor 500 is received in the space 34 in the duct 30, and the rotating shaft 501 thereof is arranged to extend lengthwise in the lateral direction. The driving motor 500 may be coupled to the duct 30 in a manner of being inserted into the space 34 in the duct 30 or may be coupled to the inner case 14. The driving motor 500 may be provided between the inner case 14 and the duct 30, that is, may be provided in a region ahead of the duct 30 within the case 12 and 14.

The internal gear 503 is formed in an arc shape. One end of the internal gear 503 is coupled to the rear surface of the first discharge vane 24. The internal gear 503 has gear-teeth formed on a portion of the inner surface thereof in the longitudinal direction so as to be engaged with the driving gear 502. Although the internal gear 503 is coupled to the rear surface of the first discharge vane 24 in this embodiment, it may alternatively be coupled to the rear surface of the suction vane 22 if the driving motor 500 is mounted at a higher position. Hereinafter, the structure in which the internal gear 503 is coupled to the rear surface of the first discharge vane 24 will be described.

The gearbox 504 may be mounted to the case 12 and 14 in a manner of being coupled to the side surface of the inner case 14.

In the state in which the suction vane 22 and the first discharge vane 24 are closed, when the driving gear 502 is rotated in one direction together with the rotating shaft 501 of the driving motor 500 by the driving force of the driving motor 500, the internal gear 503 is moved in the forward direction, and accordingly the first discharge vane 24 is rotated and opened. At the same time, the fourth gear 508 coupled to the rotating shaft 24a of the first discharge vane 24 is rotated, the second gear 506 engaged with the fourth gear 508 is rotated, the first gear 505 engaged with the second gear 506 is rotated, and the third gear 507 engaged with the first gear 505 and coupled to the rotating shaft 22a of the suction vane 22 is rotated. As a result, the suction vane 22 is opened together with the first discharge vane 24 at the same time.

In the state in which the suction vane 22 and the first discharge vane 24 are open, when the rotating shaft 501 of the driving motor 500 is rotated in the reverse direction, the internal gear 503 is moved in the backward direction, and accordingly the first discharge vane 24 is rotated and closed. At the same time, the fourth gear 508, the second gear 506, the first gear 505 and the third gear 507 are rotated in the reverse direction. As a result, the suction vane 22 and the first discharge vane 24 are closed at the same time.

Figure 4:
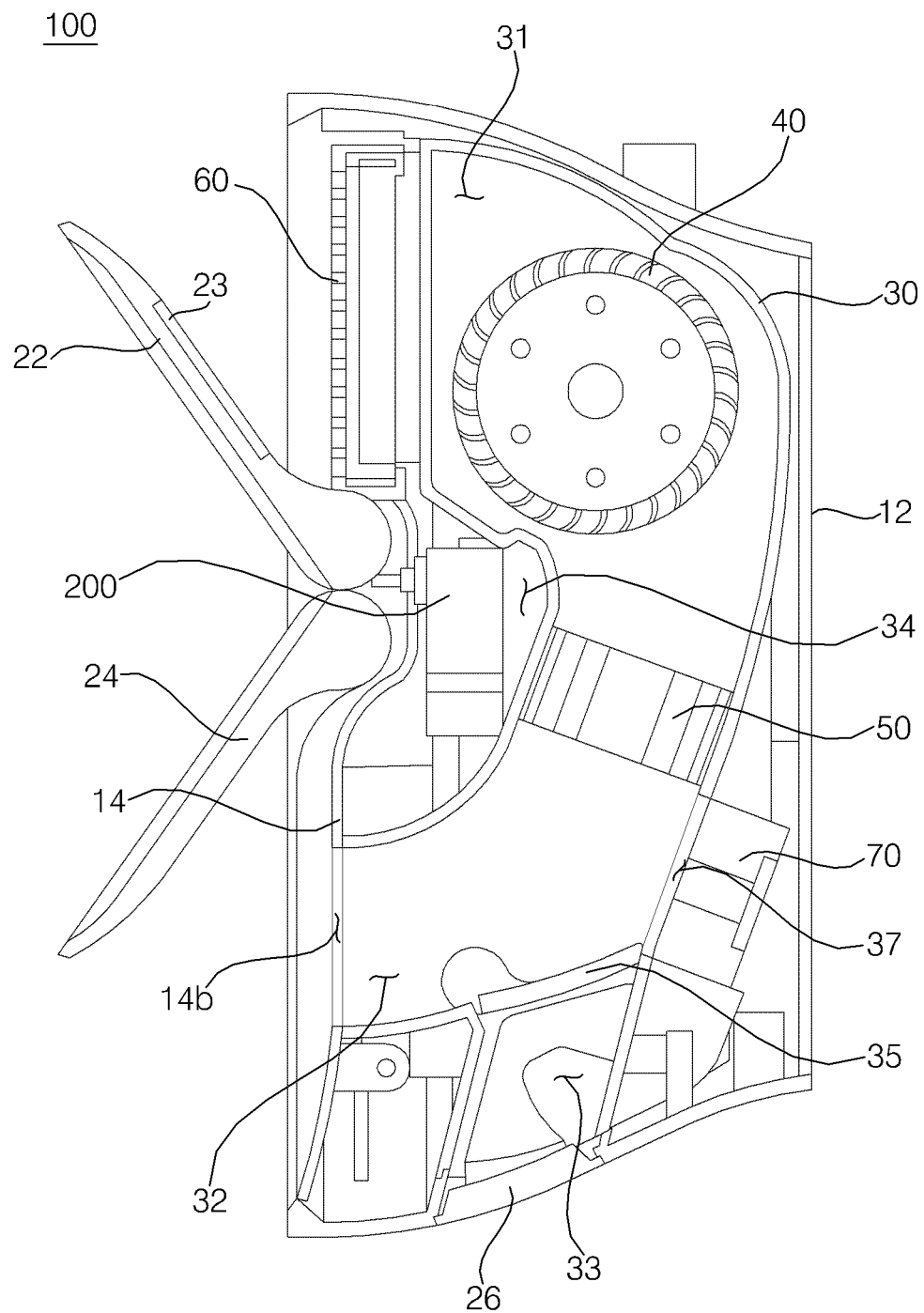
FIG. 4 is a side-sectional view of FIG. 2.
Figure 5:
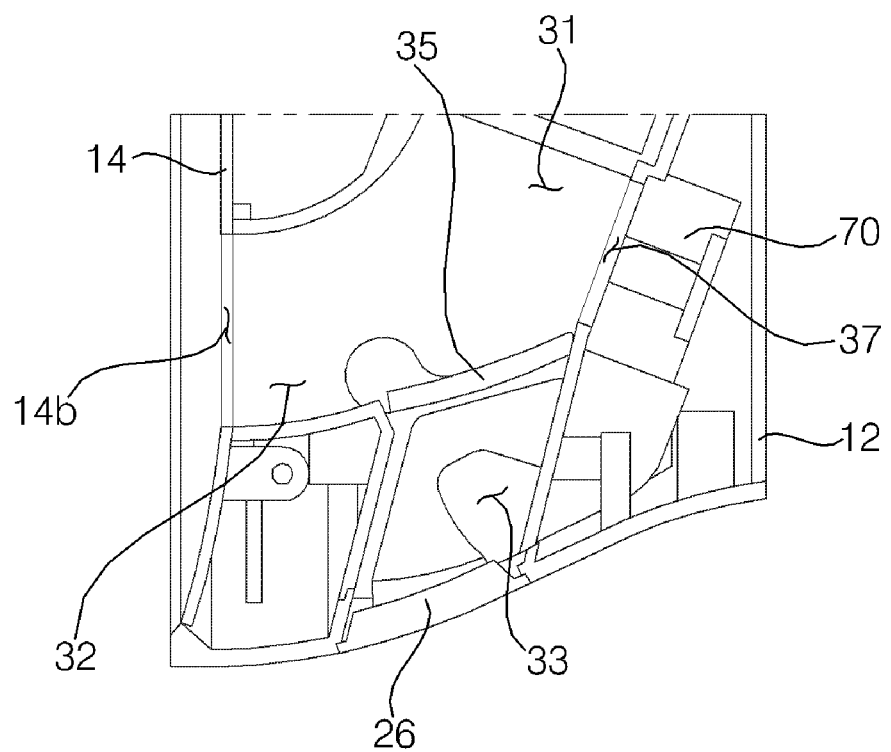
FIG. 5 is a side-sectional view of a lower portion of the bathroom management apparatus according to the embodiment of the present disclosure.
Figure 6:
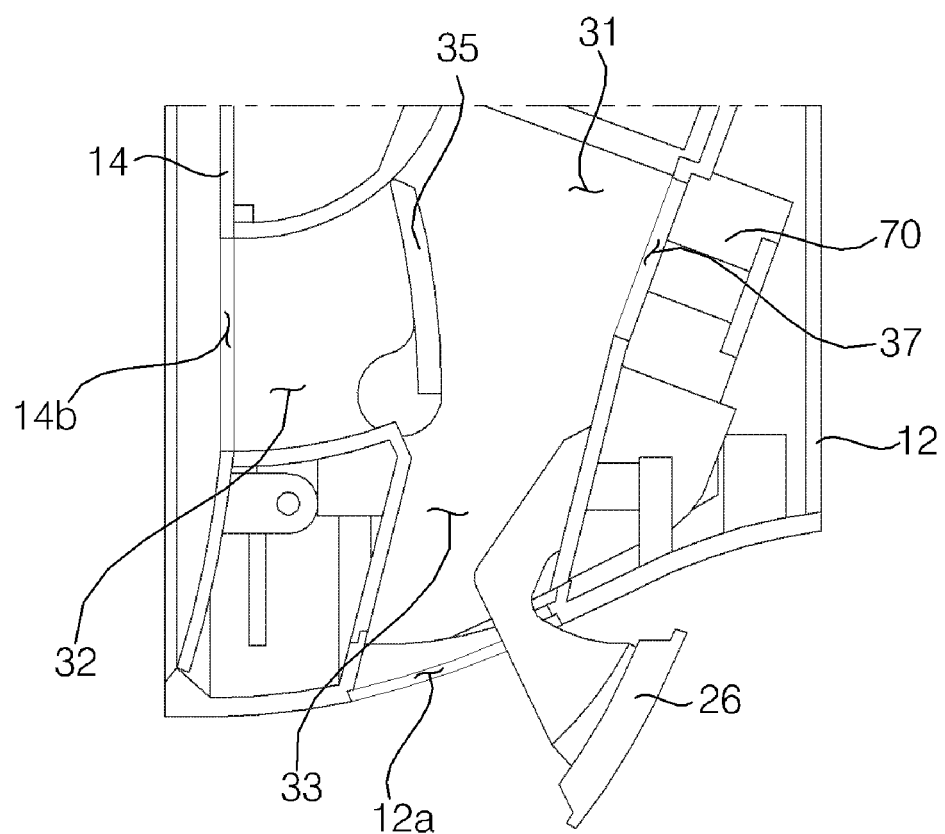
FIG. 6 is a view illustrating the state in which a second discharge vane shown in FIG. 5 is open.

Meanwhile, the ionizers 70 have been described as being mounted to the duct 30 with reference to FIGS. 3 and 4. However, the ionizers 70 are not necessarily mounted to the duct 30, as long as the ionizers 70 are mounted as close to the first sub-flow path 32 and the second sub-flow path 33 as possible. Another embodiment related to the mounting position of the ionizers 70 will now be described with reference to FIGS. 13 and 14.

Figure 13:
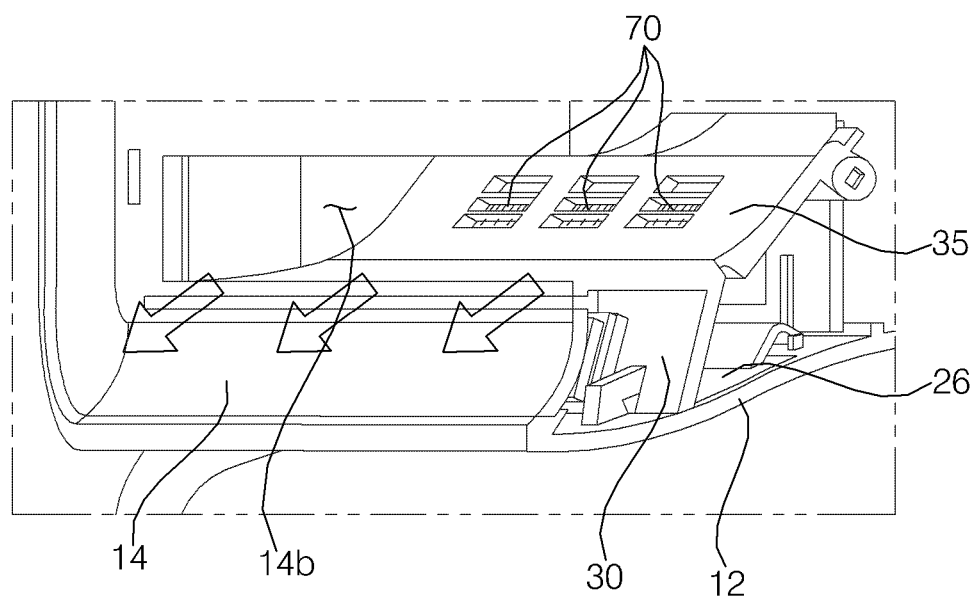
FIGS. 13 and 14 are views illustrating another embodiment of a flow-path-switching damper.
Figure 14:
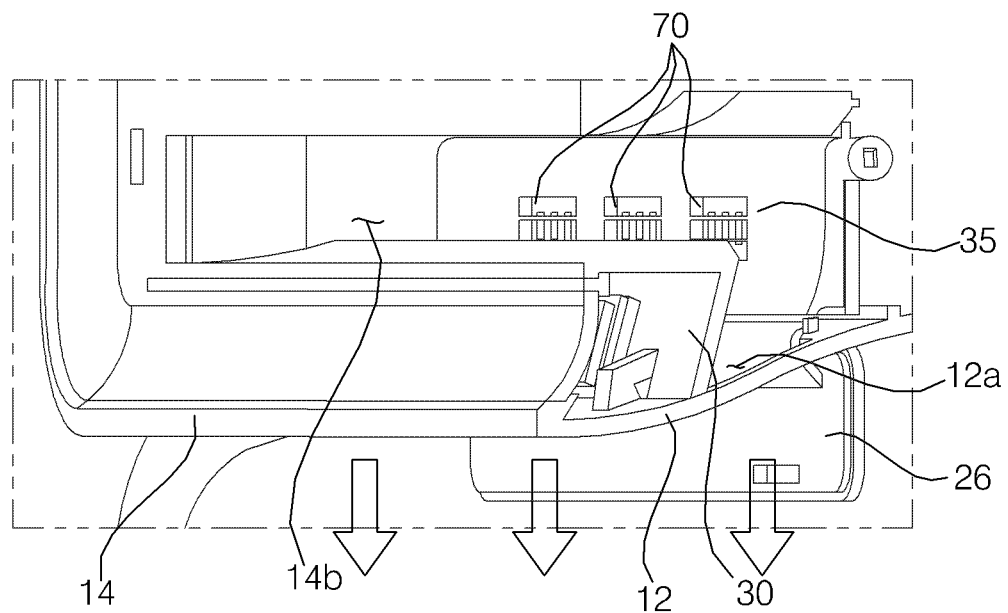

FIGS. 13 and 14 are views illustrating another embodiment of the flow-path-switching damper.

Referring to FIGS. 13 and 14, the ionizers 70 are mounted to the flow-path-switching damper 35. As shown in FIG. 13, in the state in which the second sub-flow path 33 is closed by the flow-path-switching damper 35 and the second air discharge port 12a is closed by the second discharge vane 26, the air in the main flow path 31 that has passed through the heater 50 receives the ions emitted from the ionizers 70 at the entrance of the first sub-flow path 32, and is discharged to the interior of the bathroom via the first air discharge port 14b, thereby drying and sterilizing the floor of the bathroom. As shown in FIG. 14, in the state in which the second sub-flow path 33 is opened by the flow-path-switching damper 35 and the second air discharge port 12a is opened by the second discharge vane 26, the air in the main flow path 31 that has passed through the heater 50 receives the ions emitted from the ionizers 70 at the entrance of the second sub-flow path 33, and is discharged to the interior of the bathroom via the second air discharge port 12a, thereby drying and sterilizing wet bathroom items such as a wet towel hung on the rack unit 80.

Meanwhile, the illumination device 15 has been described as being mounted to the intermediate portion 14e of the inner case 14 with reference to FIGS. 3 and 4. However, the mounting position of the illumination device 15 may be changed variously, and the reflector 23 may not be mounted to the rear surface of the suction vane 22 depending on the position of the illumination device 15. Various embodiments related to the mounting position of the illumination device 15 will now be described with reference to FIGS. 15 to 17.

Figure 15:
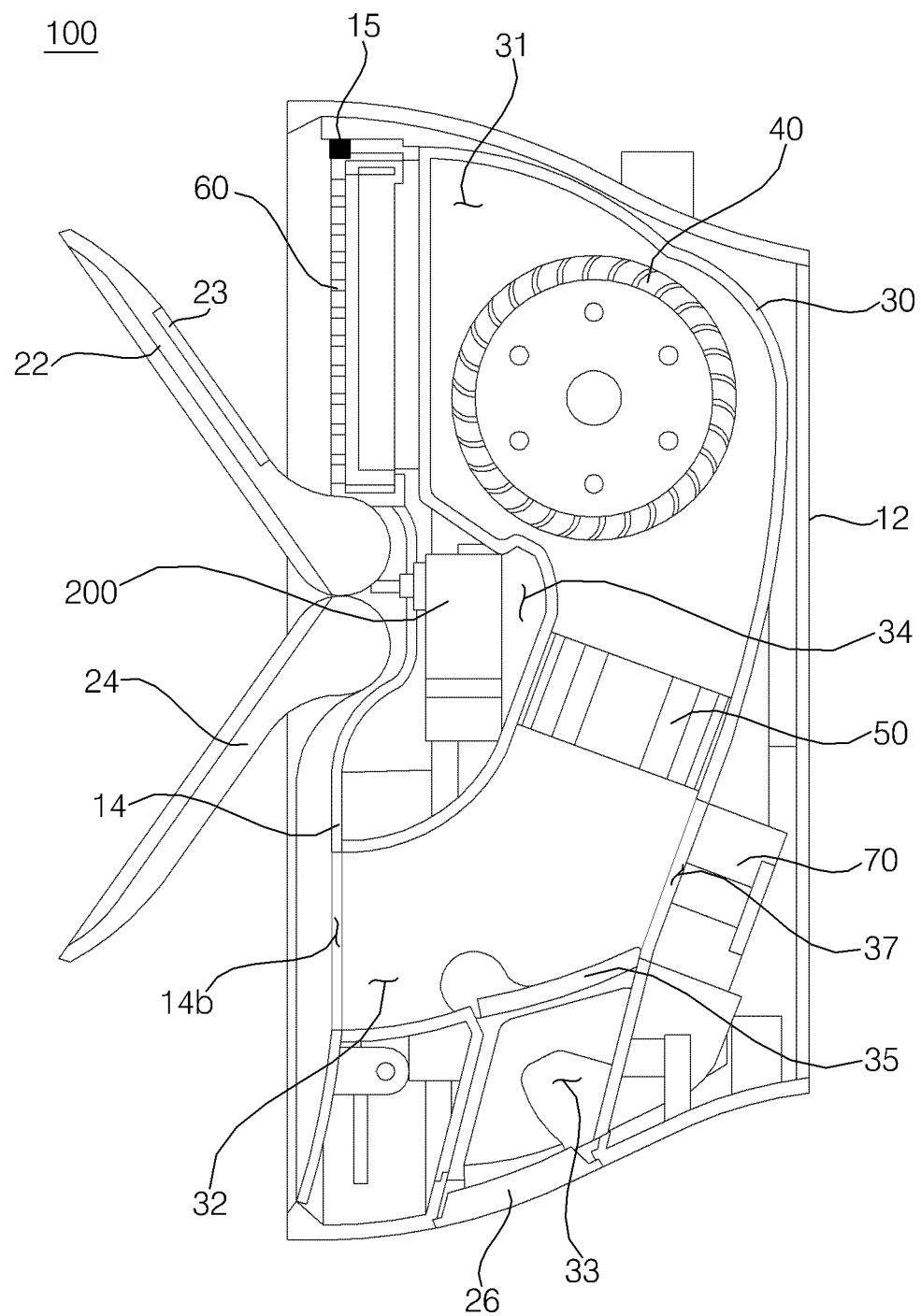
FIGS. 15 to 17 are views illustrating various embodiments related to the mounting position of an illumination device.
Figure 16:
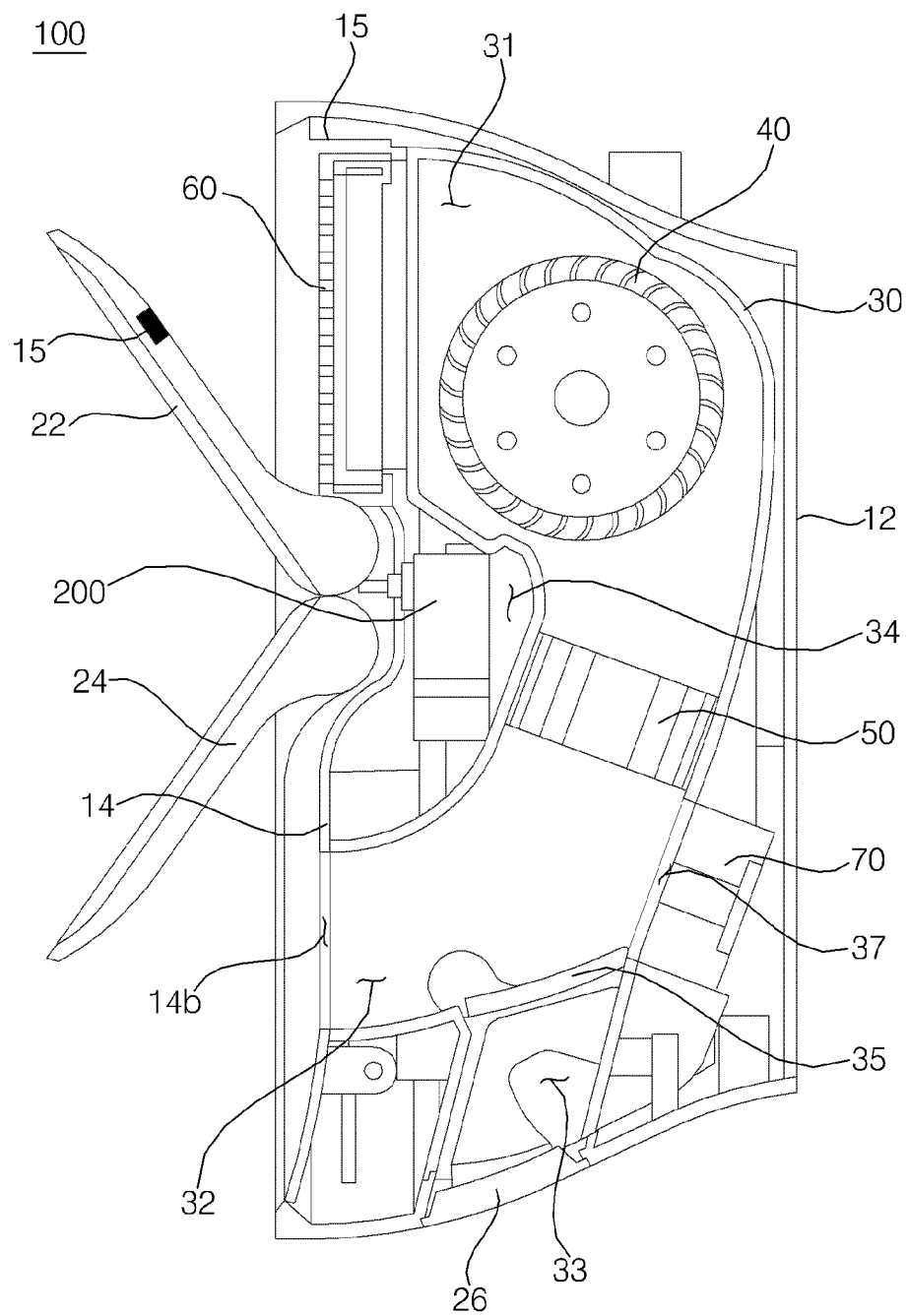
Figure 17:
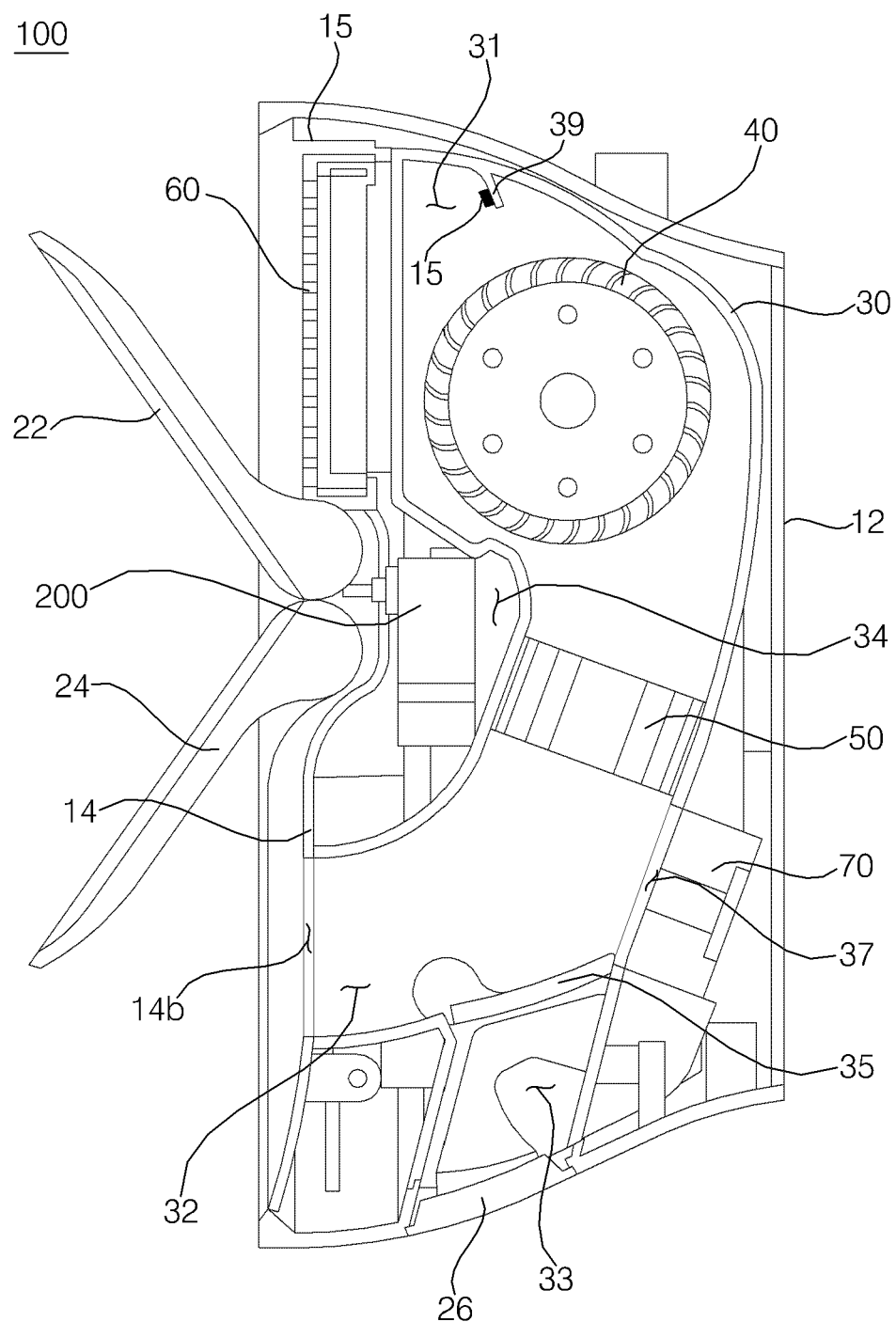

FIGS. 15 to 17 are views illustrating various embodiments related to the mounting position of the illumination device.

Referring to FIG. 15, the illumination device 15 is mounted to the upper portion 14d of the inner case 14. Specifically, the illumination device 15 is mounted to a portion of the inner case 14 that corresponds to the top of the air suction port 14a. The reflector 23 for reflecting the light generated by the illumination device 15 to the filter 60 is mounted to the rear surface of the suction vane 22.

Referring to FIG. 16, the illumination device 15 is mounted to the rear surface of the suction vane 22. The light generated by the illumination device 15 is directly radiated to the filter 60. Therefore, it is not necessary to mount the reflector 23 to the rear surface of the suction vane 22.

Referring to FIG. 17, the illumination device 15 is mounted in the duct 30. The duct 30 has a mounting portion 39 that protrudes toward the interior of the main flow path 31, and the illumination device 15 is coupled to the mounting portion 39. The light generated by the illumination device 15 is directly radiated to the filter 60. Therefore, it is not necessary to mount the reflector 23 to the rear surface of the suction vane 22.

In the case in which the illumination device 15 is mounted as illustrated in FIGS. 3, 15 and 16, the light is radiated to the filter 60 only when the suction vane 22 is in the open state. However, in the case in which the illumination device 15 is mounted in the duct 30 as illustrated in FIG. 17, even when the suction vane 22 is in the closed state, the light is radiated to the filter 60 and activates the photocatalytic material of the filter 60, and an indirect illumination effect is exhibited, thus being aesthetically pleasing when the user looks into the bathroom.

As described above, the bathroom management apparatus 100 according to the embodiment of the present disclosure is characterized in that the illumination device 15 having a function of activating the photocatalytic material of the filter 60 is capable of being mounted at various positions and being used for indirect illumination for the bathroom. An embodiment related to use of the illumination device 15 for indirect illumination for the bathroom will now be described.

Figure 18:
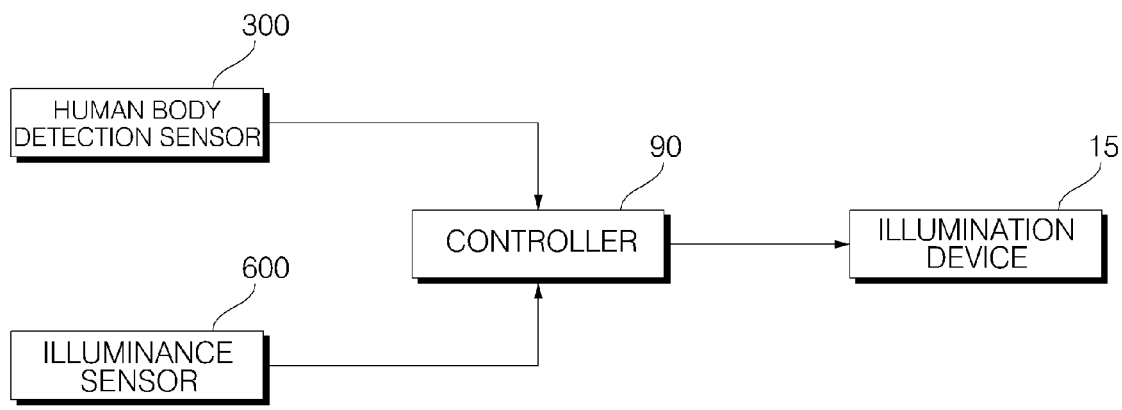
FIG. 18 is a control block diagram of the bathroom management apparatus according to the embodiment of the present disclosure.

FIG. 18 is a control block diagram of the bathroom management apparatus according to the embodiment of the present disclosure.

Referring to FIG. 18, the bathroom management apparatus 100 according to the embodiment of the present disclosure further includes a human body detection sensor 300 and an illuminance sensor 600.

The human body detection sensor 300 detects the human body and transmits the human body detection signal to the controller 90. The controller 90 turns on or off the illumination device 15 in response to the human body detection signal from the human body detection sensor 300. When the human body detection sensor 300 detects the human body and transmits the human body detection signal to the controller 90, the controller 90 may turn on the illumination device 15 in response to the human body detection signal input thereto. Conversely, when the controller 90 does not receive the human body detection signal, the controller 90 may turn off the illumination device 15. The human body detection sensor 300 may be mounted to the bathroom management apparatus 100 or may be mounted near the entrance of the bathroom.

The illuminance sensor 600 detects the illuminance outside the bathroom. In the case in which the entrance of the bathroom is located indoors, the exterior of the bathroom may be, for example, a living room, which is an indoor space provided adjacent to the bathroom. In the case in which the entrance of the bathroom is located outdoors, the exterior of the bathroom may be the outside of the building. That is, the illuminance sensor 600 detects the illuminance in the living room when it is mounted in the living room, or detects the illuminance outside the building when it is mounted outside the building. The illuminance sensor 600 detects the illuminance outside the bathroom and transmits the illuminance detection value to the controller 90. In response to the illuminance detection value of the exterior of the bathroom detected by the illuminance sensor 600, the controller 90 controls the intensity of light emitted from the illumination device 15.

Data about the intensities of light of the illumination device 15 suitable for respective illuminance values are stored in the controller 90. When the controller 90 receives an illuminance detection value from the illuminance sensor 600, the controller 90 selects an intensity of light corresponding to the illuminance detection value from the data stored therein and performs control such that the illumination device 15 emits light having the selected intensity. Therefore, the illumination device 15 emits light having an intensity equivalent to the intensity of light outside the bathroom. As a result, when the user enters the bathroom, the user does not feel glare because there is little difference between the illuminance in the bathroom and the illuminance outside the bathroom.

As described above, the bathroom management apparatus 100 according to the embodiment of the present disclosure is characterized in that the illumination device 15 is controlled so as to be automatically turned on in response to detection of the human body by the human body detection sensor 300 when the user enters the bathroom and is controlled so as to be automatically turned off when the user exits the bathroom, thereby reducing power consumption. In addition, since the illumination device 15 emits light having an intensity corresponding to the illuminance outside the bathroom, the user does not feel glare when he/she enters the bathroom.

Figure 19:
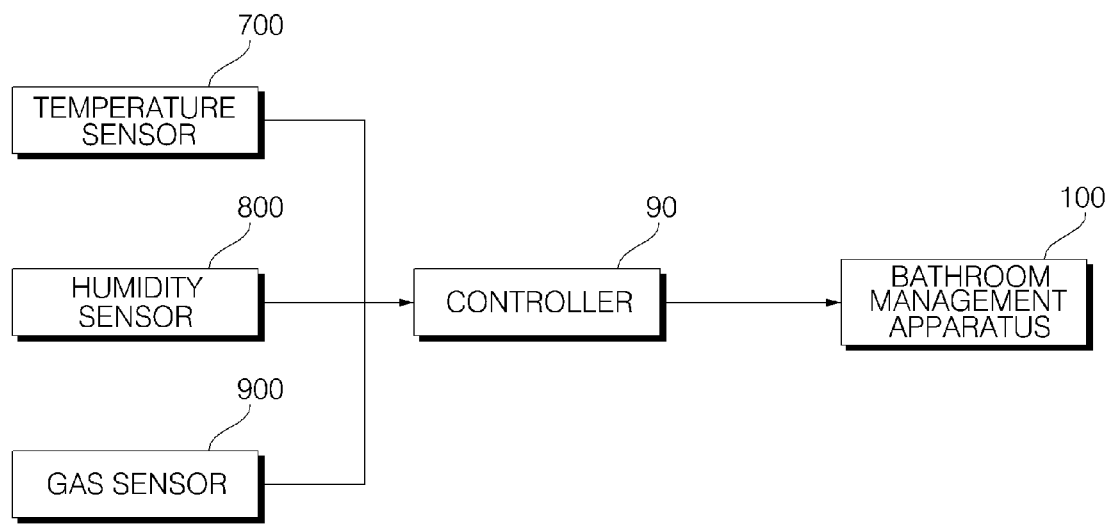
FIG. 19 is a control block diagram of the bathroom management apparatus according to the embodiment of the present disclosure.

FIG. 19 is a control block diagram of the bathroom management apparatus according to the embodiment of the present disclosure.

Referring to FIG. 19, the bathroom management apparatus 100 according to the embodiment of the present disclosure further includes a temperature sensor 700, a humidity sensor 800, and a gas sensor 900. The temperature sensor 700, the humidity sensor 800 and the gas sensor 900 may be mounted to the case 12 and 14.

The temperature sensor 700 detects the temperature in the bathroom and transmits the temperature detection value to the controller 90. The humidity sensor 800 detects the humidity in the bathroom and transmits the humidity detection value to the controller 90. The gas sensor 900 detects gas in the bathroom and transmits the gas detection value to the controller 90.

When an event (e.g. urination/defecation, a shower, a bath, cleaning, etc.) occurs in the bathroom, the controller 90 may perform control such that the bathroom management apparatus 100 operates automatically based on the detection value transmitted thereto from at least one of the temperature sensor 700, the humidity sensor 800, the gas sensor 900 and the human body detection sensor 300.

For example, when the bathroom is in the high-temperature and high-humidity state, that is, when the temperature detection value transmitted from the temperature sensor 700 is equal to or greater than a predetermined level and the humidity detection value transmitted from the humidity sensor 800 is equal to or greater than a predetermined level, the controller 90 may perform control such that the bathroom management apparatus 100 automatically performs the drying and sterilization operations with respect to the bathroom.

In addition, when the gas detection value transmitted from the gas sensor 900 is equal to or greater than a predetermined level, the controller 90 may perform control such that the bathroom management apparatus 100 automatically performs the deodorizing operation with respect to the bathroom. In an example, after the user defecates, the bathroom management apparatus 100 deodorizes the bathroom so as not to give the next user an unpleasant feeling. In another example, after the user cleans the bathroom with a bathroom cleaner, the bathroom management apparatus 100 deodorizes the bathroom so as to rapidly remove the odor of the bathroom cleaner.

Because an odor of the strong reducing gas generated from the bathroom cleaner is distinguished from other odors, the controller 90 is capable of determining a bathroom cleaning cycle based on the period at which the odor of the reducing gas is detected with the passage of time. In addition, in association with the data transmitted from the temperature sensor 700 and the humidity sensor 800, the controller 90 may inform the user of an appropriate time for cleaning the bathroom, may maintain the ventilation operation until the odor of the remaining reducing gas in the bathroom is removed, may send information about the ventilation to a device located outside the bathroom so that the user may know whether the odor of the reducing gas remains in the bathroom, or may inform the user of the number of bathroom cleanings per month or per week.

In addition, when the temperature detection value transmitted from the temperature sensor 700 is equal to or less than a predetermined level, the controller 90 may perform control such that the bathroom management apparatus 100 automatically performs the operation of supplying warm air to the interior of the bathroom. At this time, the controller 90 may maintain the warm-air-supplying operation of the bathroom management apparatus 100 until the temperature detection value transmitted from the temperature sensor 700 reaches the predetermined level, and may stop the operation of the bathroom management apparatus 100 when the temperature detection value reaches the predetermined level. When the temperature in the bathroom is low, for example, in winter, the bathroom management apparatus 100 raises the temperature in the bathroom in advance before the user enters the bathroom, thereby enabling the user to feel warm when he/she enters the bathroom.

In addition, when the temperature detection value transmitted from the temperature sensor 700 is equal to or less than the predetermined value and the human body detection signal is transmitted to the controller 90 from the human body detection sensor 300, the controller 90 may perform control such that the bathroom management apparatus 100 automatically performs the operation of supplying warm air to the interior of the bathroom. According to this control mode, since the bathroom management apparatus 100 operates only when the user enters the bathroom, power consumption may be reduced.

In addition, even though the temperature detection value transmitted from the temperature sensor 700 is equal to or less than the predetermined level, the controller 90 may not automatically drive the bathroom management apparatus 100. Only when the user selects a shower mode by manipulating at least one of the input buttons 14c, the controller 90 may drive the bathroom management apparatus 100 such that warm air is supplied to the interior of the bathroom until the temperature detection value reaches the predetermined level, thereby reducing power consumption.

The controller 90 may perform maintenance on the bathroom using historic data of the temperature detection value transmitted from the temperature sensor 700 and the humidity detection value transmitted from the humidity sensor 800.

The controller 90 may collect changes in temperature and humidity in the bathroom with the passage of time on the basis of the temperature detection value transmitted from the temperature sensor 700 and the humidity detection value transmitted from the humidity sensor 800. Upon determining that the time for which the high-humidity state is maintained exceeds a level that causes rapid generation and growth of fungi or bacteria, the controller 90 may inform the user of the necessity of bathroom cleaning or maintenance.

In the case in which a temperature sensor is additionally mounted in the living room, the controller 90 may compare the data output from the temperature sensor in the living room with the data output from the temperature sensor 700, and may perform control such that the bathroom management apparatus 100 automatically performs the operation of supplying warm air to the interior of the bathroom so that the temperature in the bathroom rises to a level equivalent to the temperature in the living room, thereby preventing the user from suffering from a shock, which may be caused by a sudden change in temperature when he/she undresses and enters the bathroom.

In the case in which a humidity sensor is additionally mounted in the living room, the controller 90 may compare the data output from the humidity sensor in the living room with the data output from the humidity sensor 800, and may inform the user of the necessity to open the door of the bathroom or of the environment in the bathroom so that the user may take action to adjust the humidity in the bathroom to a level equivalent to the humidity in the living room.

Meanwhile, because the bathroom management apparatus 100 is mounted in the bathroom, it is exposed to a high-humidity environment, and accordingly the self-sanitizing function is also important.

In the state in which the suction vane 22, the first discharge vane 24 and the second discharge vane 26 are closed, the controller 90 may drive only the heater 50 intermittently for a predetermined time period, or may drive only the blowing fan 40 intermittently for a predetermined time period, thereby drying the interior of the bathroom management apparatus 100.

When the interior of the bathroom management apparatus 100 is completely dried, the controller 90 may drive only the ionizers 70 for a predetermined time period, or may drive both the ionizers 70 and the heater 50 for a predetermined time period, thereby sterilizing the interior of the bathroom management apparatus 100.

While the interior of the bathroom management apparatus 100 is dried and sterilized, the controller 90 may recognize the change in temperature in the bathroom management apparatus 100 using the temperature detection value transmitted from the temperature sensor 700. Based on the change in temperature in the bathroom management apparatus 100, the controller 90 may determine the point of time at which the operation of the bathroom management apparatus 100 is stopped, and may stop the operation of the bathroom management apparatus 100. Further, the controller 90 may terminate the mode of sterilizing the interior of the bathroom management apparatus 100 after a predetermined time period has elapsed.

The bathroom management apparatus 100 according to the embodiment of the present disclosure has a sealing structure (or a waterproof structure), excluding the flow paths in the duct 30. Therefore, the user is capable of cleaning the bathroom management apparatus 100. For example, the user may rotate the suction vane 22 and the first discharge vane 24 to an angle of 90 degrees with respect to the inner case 14, and may clean the bathroom management apparatus 100 by spraying water to the interior thereof.

Meanwhile, the above-described bathroom management apparatus 100 according to the embodiment of the present disclosure is constructed such that the rack unit 80, on which the towel 1 or the like is hung, is coupled to the portion of the case 12 and 14 through which air is discharged. Therefore, screw anchors for the existing towel rack that has been mounted in the bathroom must be first removed, and the bathroom management apparatus 100 is mounted to the mounting portion from which the screw anchors for the existing towel rack are removed. Hereinafter, a process of mounting the bathroom management apparatus 100 according to the embodiment of the present disclosure to the wall of the bathroom will be described with reference to FIGS. 20 to 25.

Figure 20:
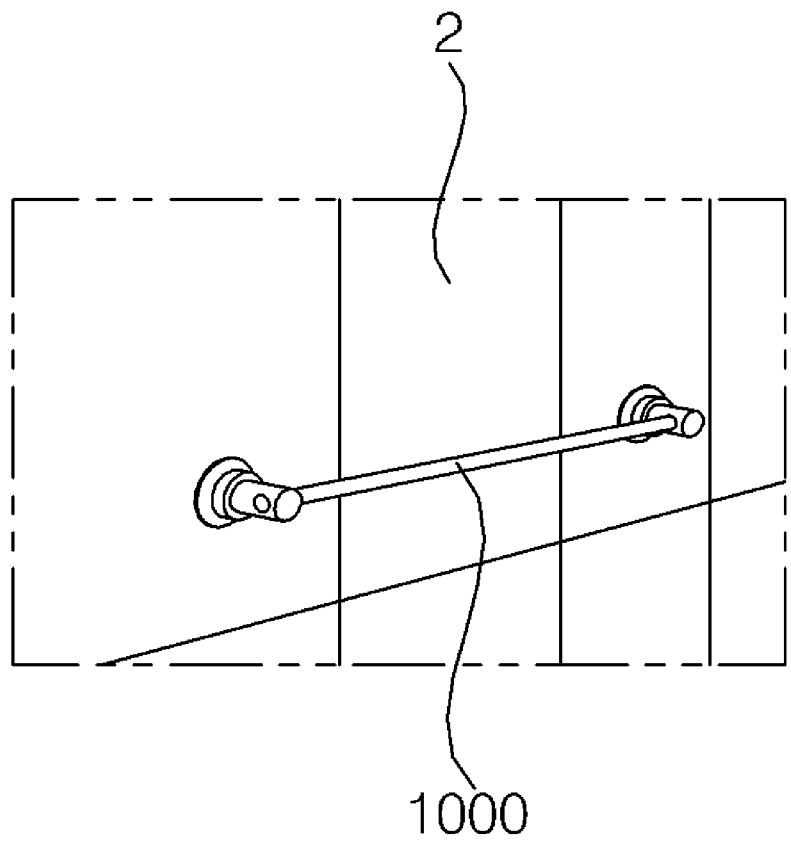
FIG. 20 is a view illustrating screw anchors for an existing towel rack that has been mounted in the bathroom.
Figure 21:
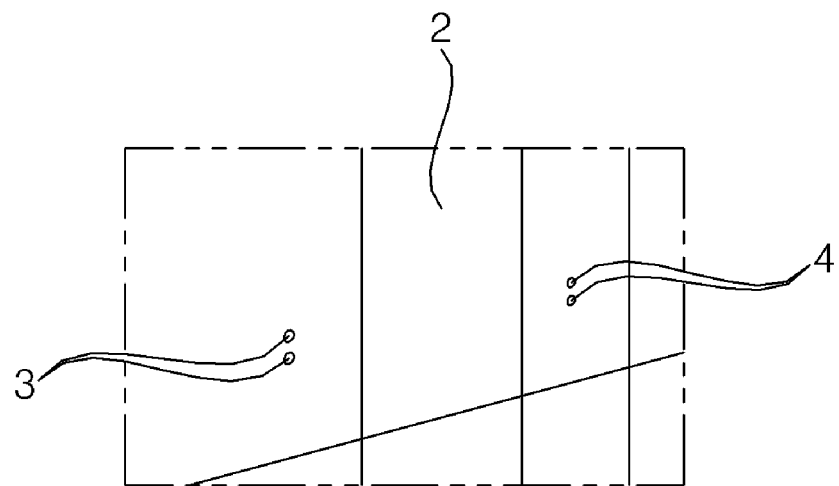
FIG. 21 is a view illustrating the state in which the screw anchors for the existing towel rack shown in FIG. 20 are removed.
Figure 22:
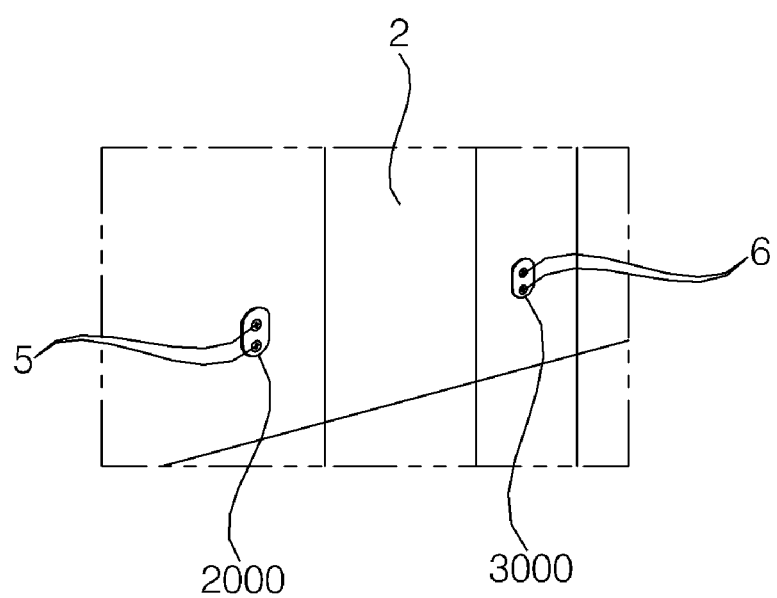
FIG. 22 is a view illustrating the state in which bracket holders are fastened into fastening holes shown in FIG. 21.
Figure 23:
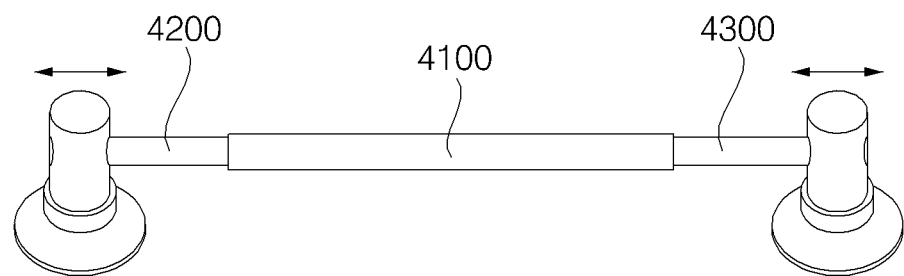
FIG. 23 is a view illustrating a support bracket.
Figure 24:
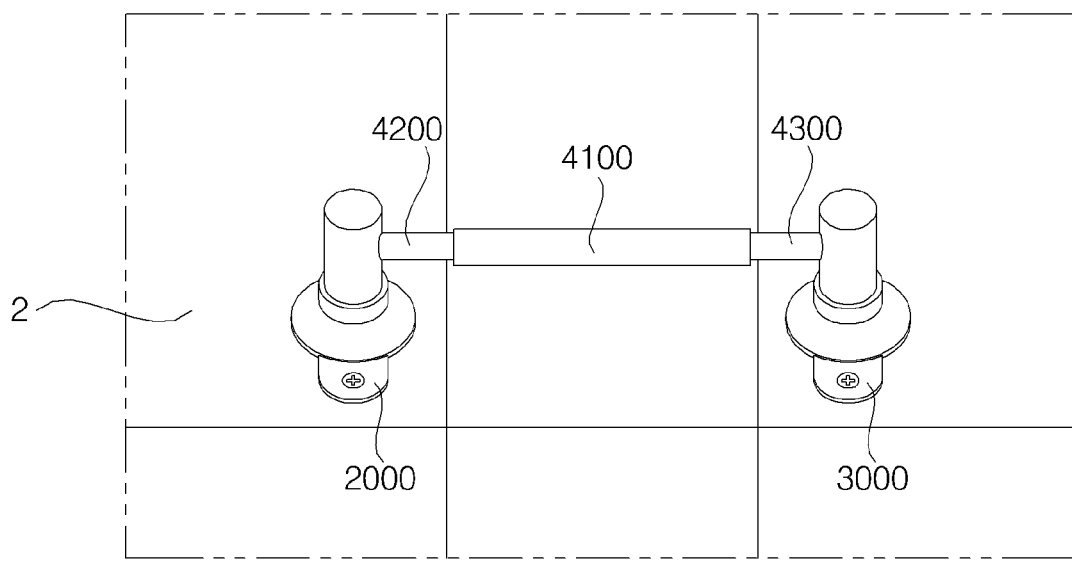
FIG. 24 is a view illustrating the state in which the support bracket shown in FIG. 23 is coupled to the bracket holders shown in FIG. 22.
Figure 25:
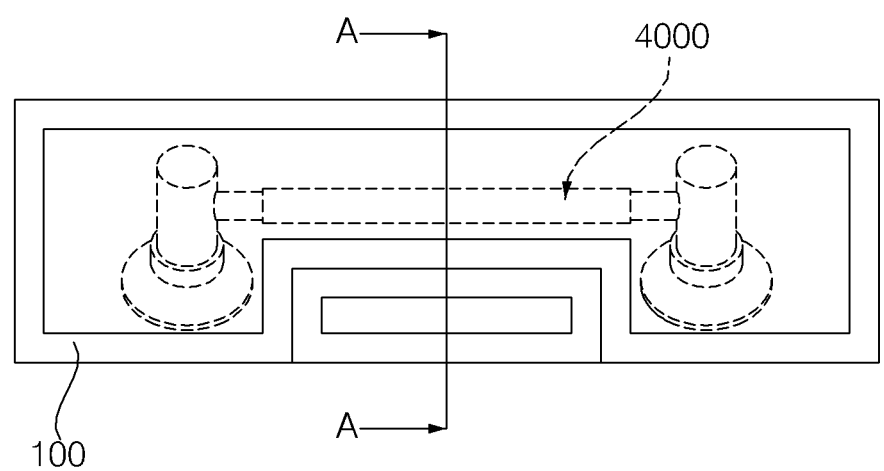
FIG. 25 illustrates a view showing the state in which the rear surface of the bathroom management apparatus according to the embodiment of the present disclosure is supported by the support bracket and a sectional view taken along line A-A.
Figure 25:
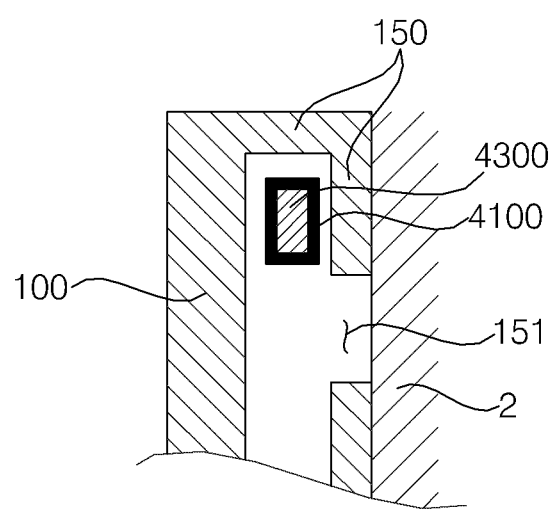

FIG. 20 is a view illustrating screw anchors for the existing towel rack that has been mounted in the bathroom. FIG. 21 is a view illustrating the state in which the screw anchors for the existing towel rack shown in FIG. 20 are removed. FIG. 22 is a view illustrating the state in which bracket holders are fastened into the fastening holes shown in FIG. 21. FIG. 23 is a view illustrating a support bracket. FIG. 24 is a view illustrating the state in which the support bracket shown in FIG. 23 is coupled to the bracket holders shown in FIG. 22. FIG. 25 illustrates a view showing the state in which the rear surface of the bathroom management apparatus according to the embodiment of the present disclosure is supported by the support bracket and a sectional view taken along line A-A.

Referring to FIGS. 20 and 21, screw anchors for the existing towel rack 1000 are mounted in the wall 2 of the bathroom. If the screw anchors for the existing towel rack 1000 are removed from the wall 2 of the bathroom, fastening holes 3 and 4 are present in the wall 2 of the bathroom. The fastening holes 3 and 4 include at least one first fastening hole 3 and at least one second fastening hole 4, which are spaced apart from each other in the lateral direction. The at least one first fastening hole 3 and the at least one second fastening hole 4 may respectively include a plurality of fastening holes. If there is no screw anchor for the existing towel rack 1000 in the wall 2 of the bathroom, for example, in a new building, it is necessary to form the fastening holes 3 and 4 in the wall 2 of the bathroom.

Referring to FIG. 22, bracket holders 2000 and 3000 are fastened into the fastening holes 3 and 4. Specifically, the bracket holders 2000 and 3000 may be fastened into the fastening holes 3 and 4 by fastening screws 5 and 6 therethrough. The bracket holders 2000 and 3000 include a first bracket holder 2000 that is to be fastened to the first fastening hole 3 and a second bracket holder 3000 that is to be fastened to the second fastening hole 4.

Referring to FIGS. 23 and 24, a support bracket 4000 is coupled to the bracket holders 2000 and 3000. The support bracket 4000 includes a main bracket 4100, a first sub-bracket 4200, which is coupled to one end of the main bracket 4100 so as to be drawn back therefrom, and a second sub-bracket 4300, which is coupled to the opposite end of the main bracket 4100 so as to be drawn back therefrom. The main bracket 4100 may be formed in a hollow pipe configuration having a rectangular-shaped cross-section. The first sub-bracket 4200 may be formed in a long rod configuration having one end having a rectangular-shaped cross-section, which is inserted into the hollow portion in the one end of the main bracket 4100 so as to be drawn back therefrom. The second sub-bracket 4300 may be formed in a long rod configuration having one end having a rectangular-shaped cross-section, which is inserted into the hollow portion in the opposite end of the main bracket 4100 so as to be drawn back therefrom.

The first sub-bracket 4200 and the second sub-bracket 4300 may be slidably coupled to the main bracket 4100. By virtue of the slidable coupling between the main bracket 4100 and the first and second sub-brackets 4200 and 4300, it is possible to draw the first and second sub-brackets 4200 and 4300 back from the main bracket 4100 by pulling them and to insert the first and second sub-brackets 4200 and 4300 into the main bracket 4100 by pushing them.

In the case in which each of the main bracket 4100, the first sub-bracket 4200 and the second sub-bracket 4300 has a circular-shaped cross-section, the main bracket 4100 may have threads formed in the inner circumferential surfaces of the hollow portions in the one end and the opposite end thereof, the first sub-bracket 4200 may have a thread formed in the outer circumferential surface of the one end thereof with which the thread of the one end of the main bracket 4100 is engaged, and the second sub-bracket 4300 may have a thread formed in the outer circumferential surface of the one end thereof with which the thread of the opposite end of the main bracket 4100 is engaged. In this case, it is possible to draw the first and second sub-brackets 4200 and 4300 back from the main bracket 4100 by rotating them in one direction and to insert the first and second sub-brackets 4200 and 4300 into the main bracket 4100 by rotating them in the reverse direction.

The overall length of the support bracket 4000 may be increased by drawing the first and second sub-brackets 4200 and 4300 back from the main bracket 4100, and may be decreased by inserting the first and second sub-brackets 4200 and 4300 into the main bracket 4100. In this way, the overall length of the support bracket 4000 may be varied.

As described above, since the overall length of the support bracket 4000 is varied, a worker is capable of adjusting the length of the support bracket 4000 in accordance with the distance between the first bracket holder 2000 and the second bracket holder 3000. After the length of the support bracket 4000 is adjusted, the first sub-bracket 4200 is coupled to the first bracket holder 2000, and the second sub-bracket 4300 is coupled to the second bracket holder 3000.

Sliding protrusions are formed on the rear surface of the portion of the first sub-bracket 4200 that is coupled to the first bracket holder 2000 and the rear surface of the portion of the second sub-bracket 4300 that is coupled to the second bracket holder 3000 so as to be inserted into gaps between the bracket holders 2000 and 3000 and the wall 2. Therefore, the first and second sub-brackets 4200 and 4300 may be coupled to the bracket holders 2000 and 3000 in a manner such that the sliding protrusions are inserted into the gaps between the bracket holders 2000 and 3000 and the wall 2 from the region above the bracket holders 2000 and 3000.

Referring to FIG. 25, after the support bracket 4000 is coupled to the bracket holders 2000 and 3000, the bathroom management apparatus 100 may be mounted to the wall 2 of the bathroom in a manner such that a support unit 150 formed on the rear surface of the bathroom management apparatus 100 is supported by the support bracket 4000. The bathroom management apparatus 100 has a slot 151 formed in a portion of the rear surface thereof that is located below the support unit 150. The support bracket 4000 is inserted into the bathroom management apparatus 100 through the slot 151 formed in the rear surface of the bathroom management apparatus 100 and supports the support unit 150, thereby completing the mounting of the bathroom management apparatus 100 to the wall of the bathroom.

Meanwhile, as described above, after the bathroom management apparatus 100 according to the embodiment of the present disclosure is mounted to the wall 2 of the bathroom, the power cable of the bathroom management apparatus 100 must be connected to a power source. Examples of connecting the power cable to a power source include a method of connecting the power cable to an outlet mounted to the wall 2 of the bathroom and a method of connecting the power cable to a power cable of a ventilation fan mounted to the ceiling of the bathroom. It is more favorable to connect the power cable of the bathroom management apparatus 100 to a power cable of a ventilation fan mounted to the ceiling of the bathroom than to connect the power cable of the bathroom management apparatus 100 to an outlet mounted to the wall because it is difficult to extend the power cable of the bathroom management apparatus 100 to the outlet along the wall of the bathroom and there is a safety problem caused by splashing water during use of the bathroom. Hereinafter, a process of connecting the power cable of the bathroom management apparatus 100 to a power cable of a ventilation fan mounted to the ceiling of the bathroom will be described with reference to FIGS. 26 to 28.

Figure 26:
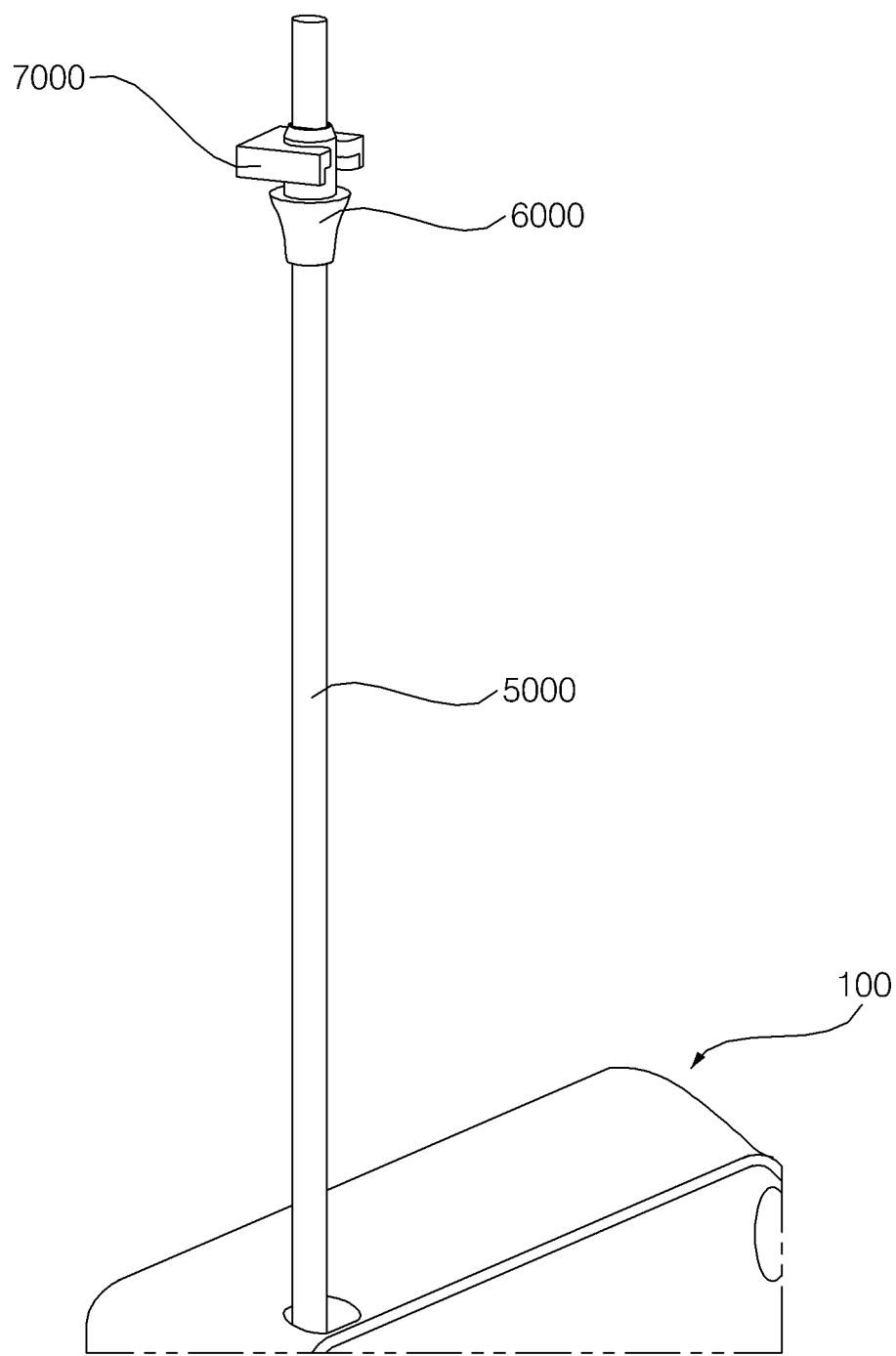
FIG. 26 is a view illustrating a cable guide coupled to the bathroom management apparatus according to the embodiment of the present disclosure.
Figure 27:
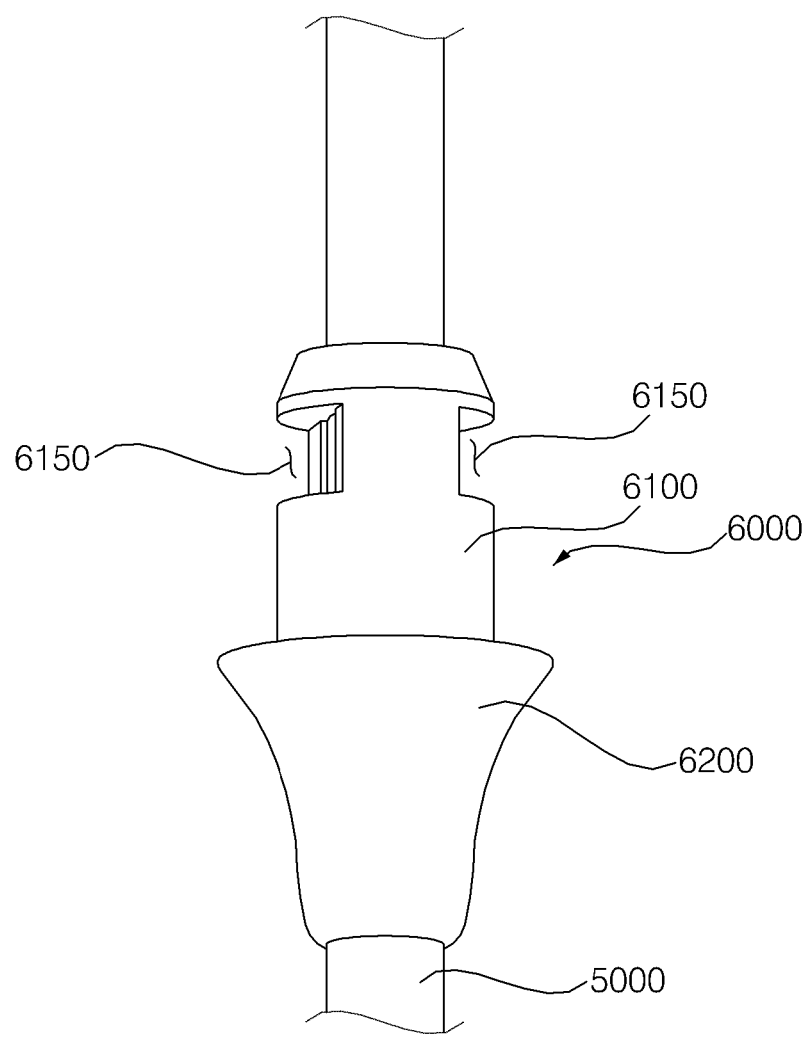
FIG. 27 is a view illustrating a guide cap shown in FIG. 26.
Figure 28:
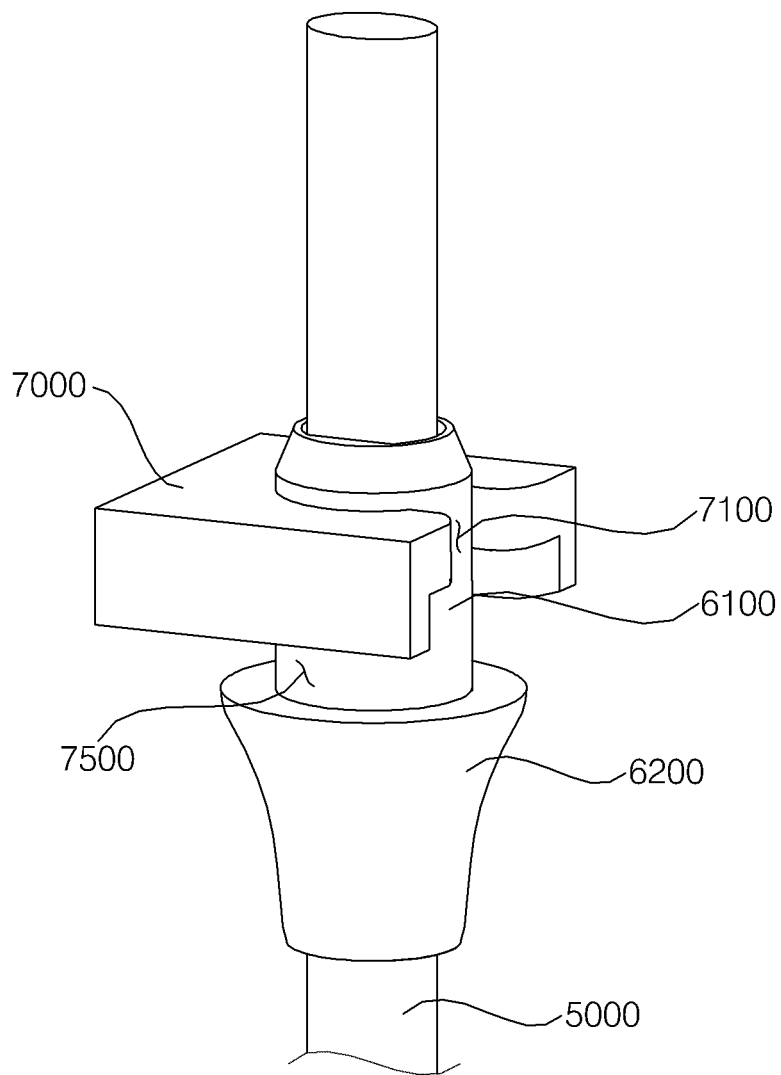
FIG. 28 is a view illustrating the state in which a cap holder is coupled to the guide cap shown in FIG. 27.

FIG. 26 is a view illustrating a cable guide coupled to the bathroom management apparatus according to the embodiment of the present disclosure, FIG. 27 is a view illustrating a guide cap shown in FIG. 26, and FIG. 28 is a view illustrating the state in which a cap holder is coupled to the guide cap shown in FIG. 27.

Referring to FIGS. 26 to 28, a cable guide 5000 is coupled at the lower end thereof to the top surface of the bathroom management apparatus 100. The cable guide 5000 is formed in a hollow pipe configuration, through which the power cable of the bathroom management apparatus 100 passes. The power cable of the bathroom management apparatus 100 passes through the cable guide 5000 and is extended to the outside through the upper end of the cable guide 5000. After the power cable of the bathroom management apparatus 100 is completely passed through the cable guide 5000, the lower end of the cable guide 5000 is coupled to the bathroom management apparatus 100. The bathroom management apparatus 100 may have a hole formed in the top surface thereof, into which the lower end of the cable guide 5000 is inserted. After the lower end of the cable guide 5000 is inserted into the hole formed in the top surface of the bathroom management apparatus 100, a gap between the hole and the cable guide 5000 is sealed by means of a sealing member such as silicon. In this way, the cable guide 5000 is coupled to the bathroom management apparatus 100.

Subsequently, a guide cap 6000 is coupled to the upper end of the cable guide 5000. The guide cap 6000 includes an insertion portion 6100 defining the upper portion thereof and a contact portion 6200 defining the lower portion thereof. The insertion portion 6100 has a smaller diameter than the upper end of the contact portion 6200. That is, the contact portion 6200 is formed such that at least the upper end thereof has a larger diameter than the insertion portion 6100.

Subsequently, a worker forms a through-hole in the ceiling, through which the insertion portion 6100 is inserted. After the insertion portion 6100 is inserted through the through-hole in the ceiling from beneath the ceiling, a cap holder 7000 is coupled to the portion of the insertion portion 6100 that is located above the ceiling, thereby securing the upper end of the cable guide 5000 to the ceiling. At this time, a worker may remove the ventilation fan from a ventilation hole formed in the ceiling, may put her/his hand into the region above the ceiling through the ventilation hole, and may couple the cap holder 7000 to the portion of the insertion portion 6100 that is located above the ceiling.

As such, when the cap holder 7000 is coupled to the guide cap 6000, the contact portion 6200 comes into contact with the bottom surface of the ceiling, thereby preventing the cable guide 5000 from moving upwards. In addition, the cap holder 7000 comes into contact with the top surface of the ceiling, thereby preventing the cable guide 5000 from moving downwards. That is, in the state in which the cap holder 7000 is coupled to the guide cap 6000, the ceiling is positioned in a space 7500 formed between the cap holder 7000 and the contact portion 6200.

The insertion portion 6100 has latching recesses 6150 formed in two opposite sides of the portion thereof that is located above the ceiling. The cap holder 7000 includes two latching portions, with an opening 7100 formed therebetween. The cap holder 7000 is coupled to the insertion portion 6100 of the guide cap 6000 in a manner such that the two latching portions of the cap holder 7000 are inserted into the latching recesses 6150 in the insertion portion 6100. In this way, the upper end of the cable guide 5000 is secured to the ceiling.

After the upper end of the cable guide 5000 is secured to the ceiling, the power cable of the bathroom management apparatus 100 that is extended to the outside through the upper end of the cable guide 5000 is connected to the power cable of the ventilation fan.

As described above, the bathroom management apparatus 100 according to the embodiment of the present disclosure is capable of drying the floor of the bathroom at an early stage with warm air discharged through the first air discharge port 14*b* and of drying wet bathroom items such as the wet towel 1 hung on the rack unit with warm air discharged through the second air discharge port 12*a*, thereby preventing fungi and bacteria from inhabiting the bathroom. In addition, it is possible to deodorize the bathroom using the filter. In addition, it is possible to sterilize the bathroom by discharging ions emitted from the ionizers 70 to the interior of the bathroom.

As is apparent from the above description, in a bathroom management apparatus according to the present disclosure, it is possible to prevent fungi and bacteria from inhabiting the bathroom by drying the interior of the bathroom at an early stage with warm air discharged through a first air discharge port and a second air discharge port.

In addition, warm air is discharged to the interior of the bathroom through the first air discharge port when a flow-path-switching damper allows a first sub-flow path to communicate with a main flow path, or is discharged to the interior of the bathroom through the second air discharge port when the flow-path-switching damper allows a second sub-flow path to communicate with the main flow path.

In addition, it is possible to kill microbes and bacteria and to prevent fungi from inhabiting the bathroom by discharging warm air containing ions, which are emitted from ionizers and are introduced into a duct, to the interior of the bathroom.

In addition, it is possible to rapidly dry a wet towel hung on a rack unit with warm air discharged through the second air discharge port, thereby preventing fungi and bacteria from inhabiting the towel.

The present disclosure discloses a bathroom management apparatus that is capable of preventing fungi and bacteria from inhabiting a bathroom by discharging warm air in two opposite directions so as to rapidly dry the bathroom.

The present disclosure discloses a bathroom management apparatus that is capable of selecting the direction in which warm air is discharged.

The present disclosure discloses a bathroom management apparatus that is capable of killing microbes and bacteria and preventing fungi from inhabiting a bathroom by discharging warm air containing negative ions to the interior of the bathroom.

The present disclosure discloses a bathroom management apparatus that is capable of preventing inhabitation of fungi and bacteria by rapidly drying wet bathroom items such as a wet towel.

A bathroom management apparatus may include a case having an air suction port formed in an upper portion of a front surface thereof, a first air discharge port formed in a lower portion of the front surface thereof, and a second air discharge port formed in a lower surface thereof, a suction vane for opening or closing the air suction port, a first discharge vane for opening or closing the first air discharge port, a second discharge vane for opening or closing the second air discharge port, a duct mounted in the case to connect the air suction port, the first air discharge port and the second air discharge port to one another, a blowing fan mounted in the duct to suck air through the air suction port and blow the air to the first air discharge port and the second air discharge port, and a heater for heating air in the duct.

The bathroom management apparatus may further include a flow-path-switching damper mounted in the duct to enable a main flow path to selectively communicate with one of a first sub-flow path and a second sub-flow path.

The bathroom management apparatus may further include ionizers mounted to the duct to emit ions into the duct.

The bathroom management apparatus may further include a rack unit on which at least one towel is hung and which is coupled to the lower surface of the case so as to be aligned with the second air discharge port.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An air blower apparatus comprising:
   a case having an air suction port formed at an upper area of a front surface thereof, a first air discharge port formed at a lower area of the front surface thereof, and a second air discharge port formed in a lower surface thereof;
   a suction vane for opening or closing the air suction port;
   a first discharge vane for opening or closing the first air discharge port;
   a second discharge vane for opening or closing the second air discharge port;
   a duct mounted between the air suction port, the first air discharge port and the second air discharge port, and provided in the case;
   a blowing fan mounted in the duct to suck air through the air suction port and blow the air to at least one of the first air discharge port or the second air discharge port; and
   a heater for heating air in the duct,
   wherein the case includes:
      a first case having an open front surface and a lower surface in which the second air discharge port is formed; and
      a second case inserted into the first case through the open front surface of the first case, the second case having an upper portion in which the air suction port is formed and a lower portion in which the first air discharge port is formed,
   wherein the duct includes:
      a main flow path in communication with the air suction port;
      a first sub-flow path branched from the main flow path and in communication with the first air discharge port; and
      a second sub-flow path branched from the main flow path and in communication with the second air discharge port,
   wherein the air blower apparatus further comprises a flow-path-switching damper mounted in the duct such that the main flow path selectively communicates with one of the first sub-flow path or the second sub-flow path, and
   wherein when the second air discharge port is closed by the second discharge vane, the flow-path-switching damper is positioned such that the main flow path communicates with the first sub-flow path.

2. The air blower apparatus according to claim 1, wherein the suction vane and the first discharge vane are rotatably coupled to the second case, and
   the second discharge vane is rotatably coupled to the duct.

3. The air blower apparatus according to claim 1, wherein the blowing fan is provided between the air suction port and the heater.

4. The air blower apparatus according to claim 1, wherein the suction vane rotates about a lower end thereof to open or close the air suction port, and
   the first discharge vane rotates about an upper end thereof to open or close the first air discharge port.

5. The air blower apparatus according to claim 1, further comprising:

a first gearbox mounted to the duct;
   a first driving gear rotatably mounted in the first gearbox to be rotated by driving force of a motor;
   a first driven gear rotatably mounted in the first gearbox to be engaged with the first driving gear and coupled to a rotating shaft of the second discharge vane; and
   a second driven gear rotatably mounted in the first gearbox to be engaged with the first driving gear and coupled to a rotating shaft of the flow-path-switching damper.

6. The air blower apparatus according to claim 1, further comprising:
   one or more ionizers mounted on the flow-path-switching damper to emit ions into the duct.

7. The air blower apparatus according to claim 1, further comprising:
   ionizers mounted to the duct to emit ions into the duct.

8. The air blower apparatus according to claim 1, further comprising:
   a filter mounted to the air suction port.

9. The air blower apparatus according to claim 8, further comprising:
   a light source mounted to the front surface of the case to generate light; and
   a reflector mounted to a rear surface of the suction vane to reflect light generated by the light source to the filter.

10. The air blower apparatus according to claim 9, wherein the light source is mounted to a prescribed area of the front surface of the case that corresponds to a region between the air suction port and the first air discharge port.

11. The air blower apparatus according to claim 9, wherein the light source is mounted to a prescribed area of the front surface of the case that corresponds to a top of the air suction port.

12. The air blower apparatus according to claim 8, further comprising:
    a light source mounted to a rear surface of the suction vane to generate light and radiate the light to the filter.

13. The air blower apparatus according to claim 8, further comprising:
    a light source mounted in the duct to generate light and radiate the light to the filter.

14. The air blower apparatus according to claim 1, further comprising:
    a discharge grill provided to the first air discharge port.

15. The air blower apparatus according to claim 1, further comprising:
    a rack or a bar to support an item, the rack or bar being coupled to the lower surface of the case so as to be aligned with the second air discharge port.

16. The air blower apparatus according to claim 1, further comprising:
    a first driving motor mounted to the case;
    a first cam coupled to a rotating shaft of the first driving motor and having a first inclined portion formed in a front surface thereof;
    a second cam formed at the suction vane and having a second inclined portion formed in a rear surface thereof so as to correspond to the first inclined portion;
    a second driving motor mounted to the case;
    a third cam coupled to a rotating shaft of the second driving motor and having a third inclined portion formed in a front surface thereof; and
    a fourth cam formed at the first discharge vane and having a fourth inclined portion formed in a rear surface thereof so as to correspond to the third inclined portion.

17. The air blower apparatus according to claim 1, further comprising:
- a driving motor provided prior to the duct within the case;
- a driving gear coupled to a rotating shaft of the driving motor;
- an internal gear coupled to one of the suction vane and the first discharge vane to be engaged with the driving gear;
- a gearbox mounted to the case;
- a first gear rotatably mounted in the gearbox;
- a second gear rotatably mounted in the gearbox to be engaged with the first gear;
- a third gear coupled to a rotating shaft of the suction vane to be engaged with the first gear; and
- a fourth gear coupled to a rotating shaft of the first discharge vane to be engaged with the second gear.

18. The air blower apparatus according to claim 1, wherein:
- the second case further includes an intermediate portion provided between the upper region and the lower region,
- the intermediate region includes a recess provided between the suction port and the first air discharge port, and
- the suction vane and the first discharge vane are rotatably coupled to the recess of the intermediate portion.

* * * * *